(12) United States Patent
Nolte et al.

(10) Patent No.: US 7,663,092 B2
(45) Date of Patent: Feb. 16, 2010

(54) METHOD AND APPARATUS FOR PHASE CONTRAST QUADRATURE INTERFEROMETRIC DETECTION OF AN IMMUNOASSAY

(75) Inventors: David D. Nolte, Lafayette, IN (US); Leilei Peng, West Lafayette, IN (US); Fred E. Regnier, West Lafayette, IN (US); Ming Zhao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 259 days.

(21) Appl. No.: 11/345,462

(22) Filed: Feb. 1, 2006

(65) Prior Publication Data

US 2007/0003436 A1 Jan. 4, 2007

Related U.S. Application Data

(60) Provisional application No. 60/649,070, filed on Feb. 1, 2005, provisional application No. 60/755,177, filed on Dec. 30, 2005.

(51) Int. Cl.
*H01J 40/14* (2006.01)
(52) U.S. Cl. .................. 250/222.2; 356/73; 422/64; 436/45
(58) Field of Classification Search .......... 250/222.2, 250/559.4; 356/72, 73, 357; 422/64, 82.05; 436/45, 165, 518

See application file for complete search history.

(56) References Cited

U.S. PATENT DOCUMENTS

| 3,796,495 A | 3/1974 | Laub |
| 4,537,861 A | 8/1985 | Elings et al. |
| 4,741,620 A | 5/1988 | Wickramasinghe |
| 4,876,208 A | 10/1989 | Gustafson et al. |

(Continued)

FOREIGN PATENT DOCUMENTS

EP 1189062 A1 3/2002

(Continued)

OTHER PUBLICATIONS

Xia, Y, et al. Non Photolithographic Methods and Fabrication of Elastomeric Stamps for Use in Microcontact Printing, Langmuir, 1996, Vo. 12, pp. 4033-4038.

(Continued)

*Primary Examiner*—Seung C Sohn
(74) *Attorney, Agent, or Firm*—Bose McKinney & Evans, LLP

(57) ABSTRACT

A phase contrast quadrature interferometric method and apparatus for determining the presence or absence of a target analyte in a sample. The method includes probing a substrate exposed to the sample with a laser beam. The substrate includes a reflecting surface with a first region having recognition molecules specific to the target analyte and a second region without recognition molecules. The method also includes probing the first and second region, and measuring time dependent intensity on a photodetector at one or both of a pair of quadrature angles of a reflected diffraction signal. The apparatus includes a laser source, a platform for receiving the planar array, an objective lens offset from the platform by approximately a focal length, and a split photodetector means for measuring a first quadrature and a second quadrature in a signal resulting from reflection of the laser beam.

29 Claims, 20 Drawing Sheets

U.S. PATENT DOCUMENTS

| | | |
|---|---|---|
| 4,899,195 A | 2/1990 | Gotoh |
| 4,975,217 A | 12/1990 | Brown |
| RE33,581 E | 4/1991 | Nicoli et al. |
| 5,122,284 A | 6/1992 | Braynin et al. |
| 5,155,549 A | 10/1992 | Dhadwal |
| 5,413,939 A | 5/1995 | Gustafson et al. |
| 5,478,527 A | 12/1995 | Gustafson et al. |
| 5,478,750 A | 12/1995 | Bernstein et al. |
| 5,494,829 A | 2/1996 | Sandstrom et al. |
| 5,497,007 A | 3/1996 | Uritsky et al. |
| 5,545,531 A | 8/1996 | Rava et al. |
| 5,581,345 A | 12/1996 | Oki et al. |
| 5,602,377 A | 2/1997 | Beller et al. |
| 5,621,532 A * | 4/1997 | Ooki et al. .................. 356/444 |
| 5,629,044 A | 5/1997 | Rubenchik |
| 5,631,171 A | 5/1997 | Sandstrom et al. |
| 5,653,939 A | 8/1997 | Hollis et al. |
| 5,700,046 A | 12/1997 | Van Doren et al. |
| 5,717,778 A | 2/1998 | Chu et al. |
| 5,736,257 A | 4/1998 | Conrad et al. |
| 5,781,649 A | 7/1998 | Brezoczky |
| 5,786,226 A | 7/1998 | Bocker et al. |
| 5,837,475 A | 11/1998 | Dorsel et al. |
| 5,843,767 A | 12/1998 | Beattie |
| 5,844,871 A | 12/1998 | Maezawa |
| 5,874,219 A | 2/1999 | Rava et al. |
| 5,875,029 A | 2/1999 | Jann et al. |
| 5,883,717 A * | 3/1999 | DiMarzio et al. ........... 356/491 |
| 5,892,577 A | 4/1999 | Gordon |
| 5,900,935 A | 5/1999 | Klein et al. |
| 5,922,617 A | 7/1999 | Wang et al. |
| 5,935,785 A | 8/1999 | Reber et al. |
| 5,945,344 A | 8/1999 | Hayes et al. |
| 5,955,377 A | 9/1999 | Maul et al. |
| 5,968,728 A | 10/1999 | Perttunen et al. |
| 5,999,262 A | 12/1999 | Dobschal et al. |
| 6,008,892 A | 12/1999 | Kain et al. |
| 6,030,581 A | 2/2000 | Virtanen |
| 6,048,692 A | 4/2000 | Maracas et al. |
| 6,060,237 A | 5/2000 | Nygren et al. |
| 6,071,748 A | 6/2000 | Modlin et al. |
| 6,099,803 A | 8/2000 | Ackley |
| 6,110,748 A | 8/2000 | Reber et al. |
| 6,121,048 A | 9/2000 | Zaffaroni et al. |
| 6,140,044 A | 10/2000 | Besemer et al. |
| 6,143,247 A | 11/2000 | Sheppard, Jr. et al. |
| 6,177,990 B1 | 1/2001 | Kain et al. |
| 6,221,579 B1 | 4/2001 | Everhart et al. |
| 6,238,869 B1 | 5/2001 | Kris et al. |
| 6,248,539 B1 | 6/2001 | Ghadiri et al. |
| 6,249,593 B1 | 6/2001 | Chu et al. |
| 6,256,088 B1 | 7/2001 | Gordon |
| 6,271,924 B1 | 8/2001 | Ngoi et al. |
| 6,287,783 B1 | 9/2001 | Maynard et al. |
| 6,287,850 B1 | 9/2001 | Besemer et al. |
| 6,312,901 B2 | 11/2001 | Virtanen |
| 6,312,961 B1 | 11/2001 | Voirin et al. |
| 6,319,468 B1 | 11/2001 | Sheppard, Jr. et al. |
| 6,319,469 B1 | 11/2001 | Mian et al. |
| 6,320,665 B1 | 11/2001 | Ngoi et al. |
| 6,327,031 B1 | 12/2001 | Gordon |
| 6,339,473 B1 | 1/2002 | Gordon |
| 6,342,349 B1 | 1/2002 | Virtanen |
| 6,342,395 B1 | 1/2002 | Hammock et al. |
| 6,345,115 B1 | 2/2002 | Ramm et al. |
| 6,350,413 B1 | 2/2002 | Reichert et al. |
| 6,355,429 B1 | 3/2002 | Nygren et al. |
| 6,368,795 B1 | 4/2002 | Hefti |
| 6,376,258 B2 | 4/2002 | Hefti |
| 6,381,025 B1 | 4/2002 | Bornhop et al. |
| 6,387,331 B1 | 5/2002 | Hunter |
| 6,395,558 B1 | 5/2002 | Duveneck et al. |
| 6,395,562 B1 | 5/2002 | Hammock et al. |
| 6,399,365 B2 | 6/2002 | Besemer et al. |
| 6,403,957 B1 | 6/2002 | Fodor et al. |
| 6,416,642 B1 | 7/2002 | Alajoki et al. |
| 6,469,787 B1 | 10/2002 | Meyer et al. |
| 6,476,907 B1 | 11/2002 | Gordon |
| 6,483,585 B1 | 11/2002 | Yang |
| 6,483,588 B1 | 11/2002 | Graefe et al. |
| 6,496,309 B1 | 12/2002 | Bliton et al. |
| 6,504,618 B2 | 1/2003 | Morath et al. |
| 6,518,056 B2 | 2/2003 | Schembri et al. |
| 6,551,817 B2 | 4/2003 | Besemer et al. |
| 6,566,069 B2 | 5/2003 | Virtanen |
| 6,584,217 B1 | 6/2003 | Lawless et al. |
| 6,591,196 B1 | 7/2003 | Yakhini et al. |
| 6,596,483 B1 | 7/2003 | Choong et al. |
| 6,602,702 B1 | 8/2003 | McDevitt et al. |
| 6,623,696 B1 | 9/2003 | Kim et al. |
| 6,624,896 B1 | 9/2003 | Neal et al. |
| 6,649,403 B1 | 11/2003 | McDevitt et al. |
| 6,653,152 B2 | 11/2003 | Challener |
| 6,656,428 B1 | 12/2003 | Clark et al. |
| 6,685,885 B2 | 2/2004 | Nolte et al. |
| 6,687,008 B1 | 2/2004 | Peale et al. |
| 6,709,869 B2 | 3/2004 | Mian et al. |
| 6,720,177 B2 | 4/2004 | Ghadiri et al. |
| 6,733,977 B2 | 5/2004 | Besemer et al. |
| 6,734,000 B2 | 5/2004 | Bhatia |
| 6,737,238 B2 | 5/2004 | Suzuki et al. |
| 6,743,633 B1 | 6/2004 | Hunter |
| 6,760,298 B2 | 7/2004 | Worthington et al. |
| 6,766,817 B2 | 7/2004 | da Silva |
| 6,770,447 B2 | 8/2004 | Maynard et al. |
| 6,783,938 B2 | 8/2004 | Nygren et al. |
| 6,787,110 B2 | 9/2004 | Tiefenthaler |
| 6,791,677 B2 | 9/2004 | Kawai et al. |
| 6,803,999 B1 | 10/2004 | Gordon |
| 6,806,963 B1 | 10/2004 | Walti et al. |
| 6,819,432 B2 | 11/2004 | Pepper et al. |
| 6,836,338 B2 | 12/2004 | Opsal et al. |
| 6,844,965 B1 | 1/2005 | Engelhardt |
| 6,847,452 B2 | 1/2005 | Hill |
| 6,878,555 B2 | 4/2005 | Anderson et al. |
| 6,897,965 B2 | 5/2005 | Ghadiri et al. |
| 6,917,421 B1 | 7/2005 | Wihl et al. |
| 6,917,432 B2 | 7/2005 | Hill et al. |
| 6,918,404 B2 | 7/2005 | da Silva |
| 6,937,323 B2 | 8/2005 | Worthington et al. |
| 6,955,878 B2 | 10/2005 | Kambara et al. |
| 6,958,131 B2 | 10/2005 | Tiefenthaler |
| 6,980,299 B1 | 12/2005 | de Boer |
| 6,980,677 B2 | 12/2005 | Niles et al. |
| 6,987,569 B2 | 1/2006 | Hill |
| 6,990,221 B2 | 1/2006 | Shams |
| 6,992,769 B2 | 1/2006 | Gordon |
| 6,995,845 B2 | 2/2006 | Worthington |
| 7,008,794 B2 | 3/2006 | Goh et al. |
| 7,012,249 B2 | 3/2006 | Krutchinsky et al. |
| 7,014,815 B1 | 3/2006 | Worthington et al. |
| 7,026,131 B2 | 4/2006 | Hurt et al. |
| 7,027,163 B2 | 4/2006 | Angeley |
| 7,031,508 B2 | 4/2006 | Lawless et al. |
| 7,033,747 B2 | 4/2006 | Gordon |
| 7,061,594 B2 | 6/2006 | Worthington et al. |
| 7,070,987 B2 | 7/2006 | Cunningham et al. |
| 7,077,996 B2 | 7/2006 | Randall et al. |
| 7,083,920 B2 | 8/2006 | Werner et al. |
| 7,087,203 B2 | 8/2006 | Gordon et al. |
| 7,088,650 B1 | 8/2006 | Worthington et al. |
| 7,091,034 B2 | 8/2006 | Virtanen |
| 7,091,049 B2 | 8/2006 | Boga et al. |
| 7,094,609 B2 | 8/2006 | Demers |

| | | |
|---|---|---|
| 7,098,041 B2 | 8/2006 | Kaylor et al. |
| 7,102,752 B2 | 9/2006 | Kaylor et al. |
| 7,106,513 B2 | 9/2006 | Moon et al. |
| 7,110,094 B2 | 9/2006 | Gordon |
| 7,110,345 B2 | 9/2006 | Worthington et al. |
| 7,118,855 B2 | 10/2006 | Cohen et al. |
| 7,141,378 B2 | 11/2006 | Miller et al. |
| 7,141,416 B2 | 11/2006 | Krutzik |
| 7,145,645 B2 | 12/2006 | Blumenfeld et al. |
| 7,148,970 B2 | 12/2006 | de Boer |
| 7,200,088 B2 | 4/2007 | Worthington et al. |
| 7,221,632 B2 | 5/2007 | Worthington |
| 2001/0055812 A1 | 12/2001 | Mian et al. |
| 2002/0001546 A1 | 1/2002 | Hunter et al. |
| 2002/0008871 A1 | 1/2002 | Poustka et al. |
| 2002/0045276 A1 | 4/2002 | Yguerabide et al. |
| 2002/0051973 A1 | 5/2002 | Delenstarr et al. |
| 2002/0058242 A1 | 5/2002 | Demers |
| 2002/0085202 A1 | 7/2002 | Gordon |
| 2002/0097658 A1 | 7/2002 | Worthington et al. |
| 2002/0106661 A1 | 8/2002 | Virtanen |
| 2002/0127565 A1 | 9/2002 | Cunningham et al. |
| 2002/0135754 A1 | 9/2002 | Gordon |
| 2002/0151043 A1 | 10/2002 | Gordon |
| 2002/0192664 A1 | 12/2002 | Nygren et al. |
| 2003/0026735 A1 | 2/2003 | Nolte et al. |
| 2003/0035352 A1 | 2/2003 | Worthington |
| 2003/0054376 A1 | 3/2003 | Mullis et al. |
| 2003/0112446 A1 | 6/2003 | Miller et al. |
| 2003/0133640 A1 | 7/2003 | Tiefenthaler |
| 2003/0134330 A1 | 7/2003 | Ravkin et al. |
| 2004/0002085 A1 | 1/2004 | Schembri et al. |
| 2004/0078337 A1 | 4/2004 | King et al. |
| 2004/0106130 A1 | 6/2004 | Besemer et al. |
| 2004/0132172 A1 | 7/2004 | Cunningham et al. |
| 2004/0150829 A1 | 8/2004 | Koch et al. |
| 2004/0155309 A1 | 8/2004 | Sorin |
| 2004/0166525 A1 | 8/2004 | Besemer et al. |
| 2004/0166593 A1 | 8/2004 | Nolte et al. |
| 2004/0223881 A1 | 11/2004 | Cunningham et al. |
| 2004/0229254 A1 | 11/2004 | Clair |
| 2004/0247486 A1 | 12/2004 | Tiefenthaler |
| 2004/0258927 A1 | 12/2004 | Conzone et al. |
| 2005/0002827 A1 | 1/2005 | McIntyre et al. |
| 2005/0003459 A1 | 1/2005 | Krutzik |
| 2005/0019901 A1 | 1/2005 | Matveeva et al. |
| 2005/0042628 A1 | 2/2005 | Rava et al. |
| 2005/0084422 A1 | 4/2005 | Kido et al. |
| 2005/0084895 A1 | 4/2005 | Besemer et al. |
| 2005/0106746 A1 | 5/2005 | Shinn et al. |
| 2005/0123907 A1 | 6/2005 | Rava et al. |
| 2005/0131745 A1 | 6/2005 | Keller et al. |
| 2005/0158819 A1 | 7/2005 | Besemer et al. |
| 2005/0176058 A1 | 8/2005 | Zaffaroni et al. |
| 2005/0191630 A1 | 9/2005 | Besemer et al. |
| 2005/0214950 A1 | 9/2005 | Roeder et al. |
| 2005/0226769 A1 | 10/2005 | Shiga |
| 2005/0248754 A1 | 11/2005 | Wang et al. |
| 2005/0254062 A1 | 11/2005 | Tan et al. |
| 2005/0259260 A1 | 11/2005 | Wakita |
| 2006/0040380 A1 | 2/2006 | Besemer et al. |
| 2006/0078935 A1 | 4/2006 | Werner et al. |
| 2006/0204399 A1 | 9/2006 | Freeman et al. |
| 2006/0210449 A1 | 9/2006 | Zoval et al. |
| 2006/0223172 A1 | 10/2006 | Bedingham et al. |
| 2006/0234267 A1 | 10/2006 | Besemer et al. |
| 2006/0256676 A1 | 11/2006 | Nolte et al. |
| 2006/0257939 A1 | 11/2006 | Demers |
| 2006/0269450 A1 | 11/2006 | Kim et al. |
| 2006/0270064 A1 | 11/2006 | Gordon et al. |
| 2007/0003436 A1 | 1/2007 | Nolte et al. |
| 2007/0003979 A1 | 1/2007 | Worthington |
| 2007/0070848 A1 | 3/2007 | Worthington et al. |
| 2007/0077599 A1 | 4/2007 | Krutzik |
| 2007/0077605 A1 | 4/2007 | Hurt et al. |

FOREIGN PATENT DOCUMENTS

| | | |
|---|---|---|
| EP | 1424549 | 6/2004 |
| WO | WO 9104489 | 4/1991 |
| WO | WO 9104491 | 4/1991 |
| WO | WO 9113353 | 9/1991 |
| WO | WO 9214136 | 8/1992 |
| WO | WO 9403774 | 2/1994 |
| WO | WO 9837238 | 8/1998 |
| WO | WO 0000265 | 1/2000 |
| WO | WO 0039584 | 7/2000 |
| WO | WO 0111310 | 2/2001 |
| WO | WO 0144441 | 6/2001 |

OTHER PUBLICATIONS

Hu, J., et al. Using Soft Lithography to Fabricate GaAs/AlGaAs Hetreostructue Field Effect Transistors, Appl. Phys.Lett.,1997 vol. 71, pp. 2020-2002.

Grzybowski, B.A., et al. Generation of Micrometer-Sized Patterns For Microanalytical Applications Using a Laser Direct-Write Method and Microcontact Printing, Anal. Chem., 1998, vol. 70, p. 4645-4652.

Martin, B.D., et al., Direct Protein Microarray Fabrication Using a Hydrogel Stamper, Langmuir, 1998, vol. 14, pp. 3971-3975.

Pompe, T., et al., Submicron Contact Printing On Silicon Using Stamp Pads, Langmuir, 1999, vol. 15, pp. 2398-2401.

Bietsch, A. and B. Michel, Conformal Contact And Pattern Stability of Stamps Used For Soft Lithography, J. Appl. Phys., 2000, vol. 88, pp. 4310-4318.

Geissler, M., et al., Mictrocontact Printing Chemical Patterns With Flat Stamps, J. Am. Chem. Soc., 2000, vol. 122, pp. 6303-6304.

Sanders, G.H.W. and A. Manz, Chip-based Microsystems For Genomic And Proteomic Analysis. Trends in Anal, Chem., 2000, vol. 19(6), pp. 3465-378.

Wang, J., Survey and Summary From DNA Biosensors To Gene Chips, Nucl. Acids Res., 2000 vol. 28(16), pp. 3011-3016.

Hagman, M., Doging Immunology On A Chip, Science, 2000, vol. 290, pp. 82-83.

Marx, J., DNA Arrays Reveal Cancer In Its Many Forms, Science, 2000, vol. 289, pp. 1670-1672.

Effenhauser, C.S., et al. Integrated Capillary Electrophoresis On Flexible Silicone Microdevices: Analysis of DNA Restriction Fragments And Detection Of Single DNA Molecules On Microchips. Anal. Chem., 1997, vol. 69, pp. 3451-3457.

He, B. and F.E. Regnier, Fabrication of Nanocolumns for Liquid Chromatography, Anal. Chem., 1998, vol. 70, p. 3790-3797.

Kricka, L.J., Miniaturization of Analytical Systems. Clin. Chem., 1998, vol. 44(9), pp. 2008-2014.

Regnier, F.E., et al. Chromatography and Electrophoresis On Chips: Critical Elements Offuture Integrated, Microfluidic Analytical Systems For Life Science. Tibtdch, 1999, vol. 17, pp. 101-106.

Ekins, R.,F. Chu, and E. Biggart, Development of Microspot Multi-Analyte Ratiometric Immunoassay Using Dual Flourescent-Labelled Antibodies. Anal. Chim. Acta, 1989, vol. 227, pp. 73-96.

Gao, H., et al., Immunosensing With Photo-Immobilized Immunoreagents On Planar Optical Wave Guides. Biosensors and Bioelecctronics, 1995, vol. 10, pp. 317-328.

Maisenholder, B., et al. A GaAs/AlGaAs-based Refractometer Platform For Integrated Optical Sensing Applications. Sensors and Actuators B, 1997, vol. 38-39, pp. 324-329.

Kunz, R.E., Miniature Integrated Optical Modules For Chemical and Biochemical Sensing. Sensors and Actuators B, 1997, vol. 38-39, pp. 13-28.

DuBendorfer, J. and R.E. Kunz, Reference Pads For Miniaure Integrated Optical Sensors. Sensors and Actuators B, 1997 vol. 38-39, pp. 1-7.

Hecht, E., Optics, 1987: Addison-Wesely publishing Co., Inc.

Scruby, C.B. and L.E. Drain, Laser Ultrasonics: Techniques and Applications. 1990, Bristol: Adam Hilger.

Nolte, D.D., et al., Adaptive Beam Combining and Interferometry Using Photorefractive Quantum Wells, J. Opt. Soc. Am. B, vol. 19, No. 2, Feb. 2001, pp. 195-205.

St. John et al., "Diffraction-Based Cell Detection Using a Microcontact Printed Antibody Grating", Analytical Chemistry, 1998, vol. 70, No. 6, pp. 1108-1111.

Morhard, F., et al., Immobilization Of Antibodies in Micropatterns For Cell Detection By Optical Diffraction. Sensors and Actuators B, 2000, vol. 70, pp. 232-242.

I. Rossomakhin and. Stepanov, Linear Adaptive Interferometers Via Diffusion Recording In Cubic Photorefractive Crystals, Opt. Commun. 86, 199-204 (1991).

Ing R.K and Monchalin, L.P., Broadband Optical Detection of Ultrasound By Two-Wave Mixing In A Photorefractive Crystal, Appl. Phys. Lett. 59, 3233-5 (1991).

Delaye, P. et al., Detection of Ultraonic Motion of a Scattering Surface by Two-Wave Mixing In a Photorefractive GaAs Crystal, Appl. Phys. Litt. 65, 932-4 (1994).

Pouet, B.F. Ing, R.K., Krishnaswanry, S. and Rover, D, Heterodyne Interferometer With Two-Wave Mixing In Photorefractive Crystals For Ultrasound Detection On Rough Surface, Appl. Phys. Lett. 69, 3782 (1996).

Montmorillon, L.A. Biaggio, I Delaye, P, Launay, J.-C., and Roosen, A, Eye Safe Large Field of View Homodyne Detection Using a Photorefractive CdTe: V Crystal, Opt. Commun. 29, 293 (1996).

P. Delaye, A. Blouin, D. Drolet, L.-A. Montmorrillong. Roosen,and J.-P Monchalin, Detection of Ultrasonice Motion of a Scattering Surface by Photorefractive InP:Fe Under An Applied dc Field, J. Opt. Soc. Am. B14, 1723-34 (1997).

I. Lahiri, L.J. Pyrak-Nolte, D.D. Nolte, M.R. Melloch, R.A. Kruger, G.D. Backer, and M. B. Klein, Laser-Based Ultrasound Detection Using Photorefractive Uantum Wells, Appl. Phys. Lett. 73, 1041-43 (1998).

S. Balassubramanian, L.Lahiri, Y. Ding, M.R. Melloch, and D.D. Nolte, Two-Wave Mixing Dynamics And Nonlinear Hot-Electom Transport In Transverse-Geometry Photorefractive Quantum Wells Studies By Moving Grantings, Appl. Phys. B. 68, 863-9 (1990).

E. Delmarche, A. Bernard, II. Schmid, B. Michel, and H. Biebuyck, Pattterned Delivery of Immonglobulines to Surface Using Microfluidic Networks, Science 276, 779-781(1997).

E. Delamarche, A. Bernard, H. Schmid, A. Bietsch, 13 Michel, and H. Biebuyck, Microfluidic Networks For Chemical Patterning of Substrates: Design and Application to Bioassays, Journal of the American Chemical Society 120, 500-508 (1998).

Kapur, Ravi et al. Streamlining the Drug Discovery Process by Integrating Miniaturization High Throughput Screening, High Content Screening, and Automation on the CellChip TM System. Biomedical Microdevices, vol. 1, No. 2, 1999, pp. 99-109.

Ekins R. et al. Multianalyte Microspot Immunoassay. The Microanalytical Compact Disk Of The Future: Clin. Chem., 1991, Vo. 37(11), p. 1955-1967.

Jenison, R., Yan, S. Haeberli, A. Polisky, B., 2001. Interference-Based Detection of Nucleic Acid Targets On Optically Coated Silicon. Nat. Biotechnol. 19, pp. 62-65.

Fattinger, C., Koller, H., Schlatter, D., Wehrli, P., 1993, The Difference Interferometer-A High Sensitive Opitcal Probel For Quantification Of Molecular-Surface Concentration; Biosens, Bioelectron 8, pp. 99-107.

Jenison, Robert et al. Silicon-based Biosensors for Rapid Detection of Protein or Nucleic Acid Targets, Clinical Chemistry, 47:10,2001 pp. 1894-1990.

Varma., M.M., et al.; High Speed Lable Free Detection By Spinning-Disk Micro-Interferometry; Biosensors & Bioelectronics, vol. 19, pp. 1371-1376, 2004.

Varma, M.M, et al.; Spinning-Disk Self-Referencing Interferrometry of Antigen-Antibody Recognition; Optics Letters, vol. 29, pp. 950-952, 2004.

Morhard et al.; Immobilization of Antibodies in Micropatterns for Cell Detection by Optical Diffraction, Sensors and Actuators B., 2000, vol. 70, pp. 232-242.

Nolte, D.D.; Semi-Insulating Semiconductor Heterostructures: Optoelectronic Properties And Applications, J.Appl.Phys. vol. 85, pp. 6269, 1999.

Brecht, A. and G. Gauglitz; Recent Developements in Optical Transducers for Chemical and Biochemical Applications. Sensors and Actuators B, 1997 vol. 38-39, pp. 1-7.

Varma, M.M. et al.; High-Speed Label-Free Multi-Analyte Detection Through Micro-Interferometry; Proc. of SPIE, vol. 496, pp. 58-64, 2003.

Ekins, R., Ligand, Assays; From Electrophoresis to Miniaturized Microaarays, Clin. Chem, 1998, vol. 44(9), pp. 2015-2030.

Somekh, Michael et al.; Scanning Heterodyne Confocal Differential Phase And Intensity Microscope, Applied Optics, vol. 34, No. 22, pp. 4857-4868; 1995.

Suddendorf, Manfred, et al.; Single-Probe-Beam Differential Amplitude And Phase-Scanning Interferometer; vol. 36, No. 25, pp. 6202-6210, 1997.

See, C.W. et al.; Scanning Differential Optical Profilometer For Simultaneous Measurement Of Amplitude and Phase Variation, Appl. Phys. Lett, vol. 53, No. 1, pp. 10-12, 1988.

Nolte, D, et al., Photorefractive Quantum Wells, 2005.

Peng, Leilei et al., Adaptive Optical biocompact Disk For Moecular Recognition, Applied Physics Letters 86, 2005.

Gruska, B, et al., Fast and Reliable Thickness and Refractive Index Measurement of Antireflection Coatings On Solar-Silicon By Ellipsometry, Sentech Instruments GmbH, Carl0Scheele-Str. 16, 12489 Berlin Germany.

Blouin, A., et al. Detection of Ultrasonic Motion of a Scattering Surface by Two-Wave Mixing in a Photorefractive GaAs Crystal, Appl. Phys. Lett., vol. 65, pp. 932-934 (1994).

Nolte, D.D., Self-Adaptive Optical Holography in Quantum Wells, Pro. Of SPIE, vol. 37:29, pp. 237-243 (1999).

Nolte, D., et al. Photorefractive Quantum Wells (Nov. 2004).

Nagarajan, R., Intensity-based segmentation of microarrays images. IEEE Trans. Med. Imaging. v22. 882-889 (2003).

Faramarzpour, N., Shirani, S. and Bondy, J., Lossless DNA microarray image compression. IEEE Conf. Signal Systems Comput. v2. 1501-1504 (2003).

Katzer, M., Kummert, F. and Sagerer, G., Methods for automatic microarray image segmentation. IEEE Trans. NanoBiosci. v2 i4. 202-214 (2003).

N. Brändle, H. Bischof, H. Lapp: "Robust DNA Microarray Image Analysis"; Machine Vision and Applications, 15 (2003), 1; 11-28.

Nagarajan, R and Peterson, C.A. [2002] Identifying Spots in Microarray Images IEEE Trans. Nanobioscience, 1(2), 78-84.

Fabri, R: "Towards non-parametric gridding of Microarray images," Digital Signal Processing, 2002. DSP 2002. 2002 14th International Conference publication, vol. 2, pp. 623-626.

Chiao-Ling Shih, Hung-Wen Chiu, "Automatic spot detection of cDNA Microarray images using mathematical morphology methods," Conference on IEEE EMBS Asian-Pacific, Oct. 2003, pp. 70-71.

MacBeath, G. and S.L. Schreiber. 2000. "Printing proteins as microarrays for high-throughput function determination." Science 289:1760-1763.

Guemouri, L., J. Ogier, and J. J. Ramsden, "Optical properties of protein monolayers during assembly." Journal of Chemical Physics 1998. 109:3265-3268.

Ostroff, R., A. Ettinger, H. La, M. Rihanek, L. Zalman, J. Meador III, A. K. Patick, S. Worland, and B. Polisky. 2001. "Rapid multiserotype detection of human rhinoviruses on optically coated silicon surfaces." J. Clin. Virol. 21: 105-117.

Jenison, R., Yang, S., Haeberli, A., and Polisky, B., "Interference-Based Detection of Nucleic Acid Targets On Optically Coated Silicon," Nature Biotechnology 19:62-65 (2001).

N. B. Sheller, S. Petrash, M.D. Foster, "Atomic Force Microscopy and X-ray Reflectivity Studies of Albumin Adsorbed onto Self-Assembled Monolayers of Hexadecyltrichlorosilane," Langmuir, 14, 4535-4544, 1998.

M. Varma, D. D. Nolte, H. D. Inerowicz, and F. E. Regnier, "Multi-Analyte Array Micro-Diffraction Interferometry," in Microarrays: Design, Fabrication and Reading, vol. 4626, B. J. B. e. al., Ed.: SPIE, 2002, pp. 69-77.

D. D. Nolte and M. R. Melloch, "Photorefractive Quantum Wells and Thin Films," in Photorefractive Effects and Materials, D. D. Nolte, Ed. Dordrecht: Kluwer Academic Publishers, pp. 373-451, 1995.

D. S. Gerber, R. Droopad, and G. N. Maracas, "A GaAs/AlGaAs Asymmetric Fabry-Perot Reflection Modulator with very High Contrast Ratio," *IEEE Phot. Tech. Lett.*, vol. 5, pp. 55-58, 1993.

M. Whitehead and G. Parry, "High-contrast reflection modulation at normal incidence in asymmetric multiple quantum well Fabry-Perot structure," *Electron. Lett.*, vol. 25, pp. 566-568, 1989.

B. J. Luff, J. S. Wilkinson, J. Piehler, U. Hollenbach, J. Ingenhoff, and N. Fabricius, "Integrated optical Mach-Zehnder biosensor," *Journal of Lightwave Technology*, vol. 16, pp. 583-592, 1998.

B. Drapp, J. Piehler, A. Brecht, G. Gauglitz, B. J. Luff, J. S. Wilkinson, and J. Ingenhoff, "Integrated optical Mach-Zehnder interferometers as simazine immunoprobes," *Sensors and Actuators B-Chemical*, vol. 39, pp. 277-282, 1997.

L. U. Kempen and R. E. Kunz, "Replicated Mach-Zehnder interferometers with focusing grating couplers for sensing applications," *Sensors and Actuators B-Chemical*, vol. 39, pp. 295-299, 1997.

V. S.-Y. Lin, K. Motesharei, K.-P. S. Dancil, M. Sailor, and M. R. Ghadiri, "A porous silicon-based optical interferometric biosensor," *Science*, vol. 278, pp. 840-843, 1997.

Y. C. Cao, R. Jin, and C. A. Mirkin, "Nanoparticles with Raman Spectroscopic Fingerprints for DNA and RNA Detection," *Science*, vol. 297, pp. 1536-1540, 2002.

T. A. Taton, C. A. Mirkin, and R. L. Letsinger, "Scanometric DNA Array Detection with Nanoparticle Probes," *Science*, vol. 289, pp. 1757-1760, 2000.

C. Gurtner, E. Tu, N. Jamshidi, R. W. Haigis, T. J. Onofrey, C. F. Edman, R. Sosnowski, B. Wallace, and M. J. Heller, "Microelectronic array devices and techniques for electric field enhanced DNA hybridization in low-conductance buffers," *Electrophoresis*, vol. 23, pp. 1543-1550, 2002.

Y. Joon Mo, J. Bell., H. Ying, M. Tirado, D. Thomas, A. H. Forster, R. W. Haigis, P. D. Swanson, R. B. Wallace, B. Martinsons, and M. Krihak, "An integrated, stacked microlaboratory for biological agent detection with DNA and immunoassays," *Biosensors & Bioelectronics*, vol. 17, pp. 605-618, 2002.

M. J. Heller, "An active microelectronics device for multiplex DNA analysis," *IEEE Engineering in Medicine & Biology Magazine*, vol. 15, pp. 100-104, 1996.

D. D. Nolte and K. M. Kwolek, "Diffraction from a Short-Cavity Fabry-Perot: Applications to Photorefractive Quantum Wells," *Opt. Commun.*, vol. 115, pp. 606-616, 1995.

R.-H. Yan, R. J. Simes, and L. A. Coldren, "Analysis and design of surface-normal Fabry-Perot electrooptic modulators," *IEEE Quant. Electron.*, vol. 25, pp. 2272-2280, 1989.

J. F. Heffernan, M. H. Moloney, J. Hegarty, J. S. Roberts, and M. Whitehead, "All optical high contrast absorptive modulation in an asymmetric Fabry-Perot etalon," *Appl. Phys. Lett.*, vol. 58, pp. 2877-2879, 1991.

A. Larsson and J. Maserjian, "Optically addressed asymmetric Fabry-Perot modulator," *Appl. Phys. Lett.*, vol. 59, pp. 3099-3101, 1991.

K. M. Kwolek, M. R. Melloch, and D. D. Nolte, "Dynamic holography in a reflection/transmission photorefractive quantum-well asymmetric Fabry-Perot," *Appl. Phys. Lett.*, vol. 65, pp. 385-387, 1994.

D. D. Nolte, "Dynamic Holographic Phase Gratings in Multiple Quantum Well Asymmetric Reflection Fabry-Perot Modulators," *Opt. Lett.*, vol. 19, pp. 819-821, 1994.

Kwolek, K.M. et al, "Photorefractive Asymmetric Fabry-Perot Quantum Wells: Transverse-filed Geometry," *Appl. Phys. Lett*, vol. 67, pp. 736-738, 1995.

B. A. Grzybowski, R. Haag, N. Bowden, and G. M. Whitesides, "Generation of micrometer-sized patterns for microanalytical applications using a laser direct-write method and microcontact printing," *Anal. Chem.*, vol. 70, pp. 4645-4652, 1998.

T. Cass and F. S. Ligler, "Immobilized Biomolecules in Analysis: A Practical Approach Series vol. 98," Oxford: Oxford, 1998.; Chapter 2: Avidin-biotin immobilization systems, pp. 15-34.

R. Guersen, I. Lahiri, M. R. Melloch, J. M. Woodall and D. D. Nolte, Transient Enhanced Intermixing of Arsenic-Rich Nonstoichiometric AlAs/GaAs Quantum Wells, Phys. Rev. B60, 10926-10934 (1999).

D. Crouse, D. D. Nolte, J. C. P. Chang, and M. R. Melloch, "Optical absorption by Ag precipitates in AlGaAs," *J. Appl. Phys.*, vol. 81, pp. 7981-7987, 1997.

G. A. Sefler, E. Oh, R. S. Rana, I. Miotkowski, A. K. Ramdas, and D. D. Nolte, "Faraday Photorefractive Effect in a Diluted Magnetic Semiconductor," *Opt. Lett.*, vol. 17, pp. 1420-1422, 1992.

J. M. McKenna, D. D. Nolte, W. Walukiewicz, and P. Becla, "Persistent holographic absorption gratings in AlSb:Se," *Appl. Phys. Lett.*, vol. 68, pp. 735-737, 1996.

R. S. Rana, E. Oh, K. Chua, a. K. Ramdas, and D. D. Nolte, "Voigtphotorefractive two-wave mixing in CdMnTe," *J. Lumin.*, vol. 60&61, pp. 56-59, 1994.

L. Peng, P. Yu, D. D. Nolte, and M. R. Melloch, "High-speed adaptive interferometer for optical coherence-domain reflectometry through turbid media," Opt. Lett. 28, 396-398 (2003).

R. M. Brubaker, Y. Ding, D. D. Nolte, M. R. Melloch, and A. M. Weiner, "Bandwidth-Limited Diffraction of Femtosecond Pulses from Photorefractive Quantum Wells," *IEEE J. Quant. Electron.*, vol. 33, pp. 2150-2158, 1997.

Y. Ding, D. D. Nolte, M. R. Melloch, and A. M. Weiner, "Real-time edge enhancement of femtosecond time-domain images by use of photorefractive quantum wells," *Opt. Lett.*, vol. 22, pp. 1101-1103, 1997.

Y. Ding, D. D. Nolte, M. R. Melloch, and A. M. Weiner, "Time-domain image processing using dynamic holography," *IEEE J. Sel. Top. Quant. Elect.*, vol. 4, pp. 332-341, 1998.

M. Dinu, D. D. Nolte, and M. R. Melloch, "Electroabsorption spectroscopy of effective-mass AIGaAs/GaAs Fibonacci superlattices," *Phys. Rev, B*, vol. 56, pp. 1987-1995, 1997.

M. Dinu, K. Nakagawa, M. R. Melloch, A. M. Weiner, and D. D. Nolte, "Broadband Low-Dispersion Diffraction of Femtosecond Pulses from Photorefractive Quantum Wells," *J. Opt. Soc. Am. B*, vol. 17, pp. 1313-1319, 2000.

Y. Ding, D. D. Nolte, Z. Zheng, A. Kanan, A. M. Weiner, and G. A. Brost, "Bandwdith Study of Volume Holography in Photorefrative InP:Fe at 1.5 microns for Frequency Domain Femtosecond Pulse Processing," *J. Opt. Soc. B*, vol. 15, pp. 2763-2768, 1998.

Y. Ding, I. Lahiri, D. D. Nolte, G. J. Dunning, and D. M. Pepper, "Electric Field Correlation of Femtosecond Pulses Using a Photo-Electromotive Force Detector," *J. Opt. Soc. Am. B*, vol. 15, pp. 2013-2017, 1998.

R. Jones, N. P. Barry, S. C. W. Hyde, P. M. W. French, K. M. Kwolek, D. D. Nolte, and M. R. Melloch, "Direct-to-Video holographic readout in quantum wells for 3-D imaging through turbid media," *Opt. Lett.*, vol. 23, pp. 103-105, 1998.

R. Jones, M. Tziraki, P. M. W. French, K. M. Kwolek, D. D. Nolte, and M. R. Melloch, "Direct-to-video holographic 3-D imaging using photorefractive multiple quantum well devices," *Optics Express*, vol. 2, pp. 439-448, 1998.

M. Tziraki, R. Jones, P. M. W. French, M. R. Melloch, and D. D. Nolte, "Photorefractive Holography for Imaging through turbid media using low coherence light," *Appl. Phys. B*, vol. 70, pp. 151-154, 1999.

M. Tziraki, R. Jones, P. French, D. Nolte, and M. Melloch, "Short-coherence photorefractive holography in multiple-quantum-well devices using light-emitting diodes," *Appl. Phys. Lett.*, vol. 75, pp. 363-365, 1999.

I. Lahiri, D. D. Nolte, M. R. Melloch, and M. B. Klein, "Oscillatory mode coupling and electrically strobed gratings in photorefractive quantum-well diodes," *Optics Lett.*, vol. 23, pp. 49-51, 1998.

I. Lahiri, L. J. Pyrak-Nolte, D. D. Nolte, and M. R. Melloch, "Transient Dynamics During Two-Wave Mixing in Photorefractive Quantum Well Diodes using Moving Gratings," *Opt. Express*, vol. 2, pp. 432-438, 1998.

C.-C. Wang, R. A. Linke, D. D. Nolte, M. R. Melloch, and S. Trivedi, "Enhanced detection bandwidth for optical doppler frequency measurements using moving space charge field effects in GaAs multiple quantum wells," *Appl. Phys. Lett.*, vol. 70, pp. 2034-2036, 1997.

C. C. Wang, R. A. Linke, D. D. Nolte, M. R. Melloch, and S. Trivedi, "Signal strength enhancement and bandwidth tuning in moving space charge field photodetectors using alternating bias field," *Appl. Phys. Lett.*, vol. 72, pp. 100-102, 1998.

D. M. Pepper, G. J. Dunning, M. P. Chiao, T. R. O'Meara, P. V. Mitchell, I. Lahiri, and D. D. Nolte, "Characterization of the photo-EMF response for laser-based ultrasonic sensing under simulated industrial conditions," *Rev. Prog. Quant. Nondestruct. Eval.*, vol. 17, pp. 627-634, 1998.

D. D. Nolte, *Mesoscopic Pointlike Defects in Semiconductors: Deep-level Energies*, Phys. Rev. B 58, 7994-8001 (1998).

M. Dinu, I. Miotkowski and D. D. Nolte, *Magnetic Quenching of Time-Reversed Light in Photorefractive Diluted Magnetic Semiconductors*, Phys. Rev. B 58, 10435 (1998).

S. Balasubramanian, S. W. Mansour, M. R. Melloch and D. D. Nolte, *Vacancy diffusion Kinetics in arsenic-rich nonstoichiometric AlAs/GaAs heterostructures*, Phys. Rev. B 63, 033305-1-033305-3 (2000).

David D. Nolte, Manoj M. Varma, Leilei Peng, Halina D. Inerowicz, Fred E. Regnier, *Spinning-disk laser interferometers for immunoassays and proteomics: the BioCD* in Proc. SPIE vol. 5328,, Microarrays and Combinatorial Techniques: Design, Fabrication, and Analysis II; Dan V. Nicolau, Ramesh Raghavachari; Eds., p. 41-48 (2004).

Manoj M. Varma, Halina D. Inerowicz, Fred E. Regnier, David D. Nolte, *Real-time spinning-disk-interferometric immunoassays*, in Proc. SPIE vol. 5328, Microarrays and Combinatorial Techniques: Design, Fabrication, and Analysis II; Dan V. Nicolau, Ramesh Raghavachari; Eds., p. 62-68 (2004).

T. Jensen, L. Kelly, A. Lazarides, and G. C. Schatz, "Electrodynamics of noble metal nanoparticles and nanoparticle clusters," *Journal of Cluster Science*, vol. 10, pp. 295-317, 1999.

H. Kuwata, H. Tamaru, K. Esumi, and K. Miyano, "Resonant light scattering from metal nanoparticles: Practical analysis beyond Rayleigh approximation," *Applied Physics Letters*, vol. 83, pp. 4625-4627, 2003.

M.J. Jory, P. S. Cann, J. R. Sambles, and E. A. Perkins, "Surface-plasmon-enhanced light scattering from microscopic spheres," *Applied Physics Letters*, vol. 83, pp. 3006-3008, 2003.

K.L. Kelly, E. Coronado, L. L. Zhao, and G. C. Schatz, "The optical properties of metal nanoparticles: The influence of size, shape, and dielectric environment," *Journal of Physical Chemistry B*, vol. 107, pp. 668-677, 2003.

P. Chakraborty, "Metal nanoclusters in glasses as non-linear photonic materials," *Journal of Materials Science*, vol. 33, pp. 2235-2249, 1998.

S. J. Oldenburg, S. L. Westcott, R. D. Averitt, and N. J. Halas, "Surface enhanced Raman scattering in the near infrared using metal nanoshell substrates," *Journal of Chemical Physics*, vol. 111, pp. 4729-4735, 1999.

P. Mulvaney, "Surface plasmon spectroscopy of nanosized metal particles," *Langmuir*, vol. 12, pp. 788-800, 1996.

H.F. Ghaemi, T. Thio, D. E. Grupp, T. W. Ebbesen, and H. J. Lezec, "Surface plasmons enhance optical transmission through subwavelength holes," *Physical Review B*, vol. 58, pp. 6779-6782, 1998.

M. Minunni and M. Mascini, "Detection of Pesticide in Drinking-Water Using Real-Time Biospecific Interaction Analysis (Bia)," *Analytical Letters*, vol. 26, pp. 1441-1460, 1993.

C. Mouvet, R. D. Harris, C. Maciag, B. J. Luff, J. S. Wilkinson, J. Piehler, A. Brecht, G. Gauglitz, R. Abuknesha, and G. Ismail, "Determination of simazine in water samples by waveguide surface plasmon resonance," *Analytica Chimica Acta*, vol. 338, pp. 109-117, 1997.

A. Rasooly, "Surface plasmon resonance analysis of staphylococcal enterotoxin B in food," *Journal of Food Protection*, vol. 64, pp. 37-43, 2001.

G. Sakai, K. Ogata, T. Uda, N. Miura, and N. Yamazoe, "A surface plasmon resonance-based immunosensor for highly sensitive detection of morphine," *Sensors and Actuators B-Chemical*, vol. 49, pp. 5-12, 1998.

G. Sakai, S. Nakata, T. Uda, N. Miura, and N. Yamazoe, "Highly selective and sensitive SPR immunosensor for detection of methamphetamine," *Electrochimica Acta*, vol. 44, pp. 3849-3854, 1999.

E. Kretschmann and H. Raether, "Radiative Decay of Non Radiative Surface Plasmons Excited by Light," *Zeitschrift Fur Naturforschung Part a-Astrophysik Physik Und Physikalische Chemie*, vol. A 23, pp. 2135-2136, 1968.

A. Otto, "Excitation of Nonradiative Surface Plasma Waves in Silver by Method of Frustrated Total Reflection," *Zeitschrift Fur Physik*, vol. 216, pp. 398-410, 1968.

J. Homola, S. S. Yee, and G. Gauglitz, "Surface plasmon resonance sensors: review," Sensors and Actuators B-Chemical, vol. 54, pp. 3-15, 1999.

M. Malmqvist, "BIAcore: an affinity biosensor system for characterization of biomolecular interactions," *Biochemical Society Transactions*, vol. 27, 1999.

M. Fivash, E. M. Towler, and R. J. Fisher, "BIAcore for macromolecular interaction," Current Opinion in Biotechnology, vol. 9, pp. 97-101, 1998.

L.D. Roden and D. G. Myszka, "Global analysis of a macromolecular interaction measured on BIAcore," Biochemical and Biophysical Research Communications, vol. 225, pp. 1073-1077, 1996.

C.F. R. Mateus, M. C. Y. Huang, B. T. Cunningham, and C. J. Chang-Hasnain, "Compact label-free biosensor using VCSEL-based measurement system," Ieee Photonics Technology Letters, vol. 16, pp. 1712-1714, 2004.

P. Y. Li, L. Bo, J. Gerstenmaier, and B. T. Cunningham, "A new method for label-free imaging of biomolecular interactions," Sensors and Actuators B-Chemical, vol. 99, pp. 6-13, 2004.

G. Walter, K. Bussow, A. Lueking, and J. Glokler, "High-throughput protein arrays: prospects for molecular diagnostics," Trends in Molecular Medicine, vol. 8, pp. 250-253, 2002.

J.B. Pendry, L. Martin-Moreno, and F. J. Garcia-Vidal, "Mimicking surface plasmons with structured surfaces," Science, vol. 305, pp. 847-848, 2004.

A.G. Brolo, R. Gordon, B. Leathem, and K. L. Kavanagh, "Surface plasmon sensor based on the enhanced light transmission through arrays of nanoholes in gold films," Langmuir, vol. 20, pp. 4813-4815, 2004.

J. A. Coy, D. D. Nolte, G. J. Dunning, D. M. Pepper, B. Pouet, G. D. Bacher, and M. B. Klein, "Asymmetric Interdigitated MSM Contacts for Improved Adaptive Photo-EMF Detectors," J. Opt. Soc. Am. B, vol. 17, pp. 697-704, 1999.

J. Coy, F. Stedt, I. Lahiri, M. Melloch, and D. Nolte, "Exciton electroabsorption moments and sum rules," Opt. Commun., vol. 176, pp. 17-29, 2000.

R. S. Rana, E. Oh, K. Chua, A. K. Ramdas, and D. D. Nolte, "Magneto-photorefractive effects in a diluted magnetic semiconductor," *Phys. Rev. B*, vol. 49, pp. 7941-7951, 1994.

D. D. Nolte, I. Lahiri, J. McKenna, F. R. Steldt, J. C. P. Chang, M. R. Melloch, and J. M. Woodall, "Wannier excitons in a Coulomb Cage," presented at 23rd Int. Conf. Phys. Semicond., Vancouver, Canada, 1994.

D. D. Nolte, J. A. Coy, G. J. Dunning, D. M. Pepper, M. P. Chiao, G. D. Bacher, and M. B. Klein, "Enhanced responsivity of non-steady-state photoinduced electromotive force sensors using asymmetric interdigitated contacts," Opt. Lett., vol. 24, pp. 342-344, 1999.

D. M. Pepper, G. J. Dunning, D. D. Nolte, J. Coy, M. B. Klein, G. D. Bacher, and B. Pouet, "Enhanced Responsivity of Photo-Induced-emf Laser Ultrasound Sensors Using Asymmetric Interdigitated Contacts," in Review of Progress in Quantitative Nondestructive Evaluation, vol. 19, D. O. Thompson and D. E. Chimenti, Eds. New York: American Institute of Physics Press, 2000, pp. 2013-2020.

Technology paper entitled "Grating-Coupled Surface Plasmon Resonance (GCSPR)"—printed from HTS Biosystems Technologies website (www.htsbiosystems.com/technology/gcspr.htm) on May 2, 2005.

B. Cunningham, P. Li, and J. Pepper, "Colorimetric resonant reflection as a direct biochemical assay technique," Sensors and Actuators B, vol. 81, pp. 316-328, 2002.

Polizzi, M.A., Plocinik, R.M., and Simpson, G.J., "Ellipsometric Approach for the Real-Time Detection of Label-Free Protein Adsorption by Second Harmonic Generation," J. Am. Chem. Soc., 126, 15, 5001-5007, 2004.

Plocinik, R. M.; Simpson, G. J., Polarization characterization in surface second harmonic generation by nonlinear optical null ellipsometry. Analytica Chimica Acta 2003, 496, (1-2), 133-142.

P. B. Luppa, L. J. Sokoll, and D. W. Chan, "Immunosensors—principles and applications to clinical chemistry," *Clinica Chimica Acta*, vol. 314, pp. 1-26, 2001.

C. L. Tucker, J. F. Gera, and P. Uetz, "Towards an understanding of complex protein networks," *Trends in Cell Biology*, vol. 11, pp. 102-106, 2001.

P. Uetz and R. L. Finley, "From protein networks to biological systems," *Febs Letters*, vol. 579, pp. 1821-1827, 2005.

G. Gauglitz, "Direct optical sensors: principles and selected applications," Analytical And Bioanalytical Chemistry, vol. 381, pp. 141-155, 2005.

S. P. Balk, Y.-J. Ko, and G. J. Bubley, "Biology of Prostate-specific antigen," J. Clin. Onc., vol. 21, pp. 383-391, 2003.

Wang, M.C., Papsidero, L.D., Kuriyama, M., Valenzuela, G.P. and Chu, T.M. 1981. Prostate antigen: A new potential marker for prostatic cancer. *The Prostate* 2: 89-96.

Musundi et al., "Approaching Real-Time Molecular Diagnostics: Single-Pair Fluorescence Resonance Energy Transfer (spFRET) Detection for the Analysis of Low Abundant Point Mutations in K-ras Oncogenes," J Am Chem Soc. Jun. 11, 2003;125(23):6937-45.

Lovgren J, Valtonen-Andre C, Marsal K, et al: Measurement of prostate-specific antigen and human glandular kallikrein 2 in different body fluids. J. Androl. 20:348-355, 1999.

J. Homola, "Present and future of surface plasmon resonance biosensors," Analytical And Bioanalytical Chemistry, vol. 377, pp. 528-539, 2003.

Konstantinos Blekas, Nikolas P. Galatsanos, Aristidis Likas, Isaac E. Lagaris: Mixture model analysis of DNA microarray images. IEEE Trans. Med. Imaging 24(7): 901-909 (2005).

Peter Bajcsy: Gridline: automatic grid alignment DNA microarray scans. IEEE Transactions on Image Processing 13(1): 15-25 (2004).

T.W. Ebbesen, H. J. Lezec, H. F. Ghaemi, T. Thio, and P. A. Wolff, "Extraordinary optical transmission through sub-wavelength hole arrays," *Nature*, vol. 391, pp. 667-669, 1998.

D.A. Genov, A. K. Sarychev, V. M. Shalaev, and A. Wei, "Resonant field enhancements from metal nanoparticle arrays," *Nano Letters*, vol. 4, pp. 153-158, 2004.

V. Koubova, E. Brynda, L. Karasova, J. Skvor, J. Homola, J. Dostalek, P. Tobiska, and J. Rosicky, "Detection of foodborne pathogens using surface plasmon resonance biosensors," Sensors and Actuators B-Chemical, vol. 74, pp. 100-105, 2001.

Abe, Takao, et al.; Microroughness Measurements on Polished Silicon Wafers. Jpn. J. Appl. Phys., vol. 31, pp. 721-728, 1992.

Nolte, D.D. et al.; Spinning-Disk Interferometry The BioCD; Optics & Photonics News, pp. 48-53, 2004.

Ding, Y., et al.; Femtosecnd Pulse Shaping By Dynamic Holograms In Photorefractive Multiple Quantum Wells; Optical Society of America, pp. 718-720; 1997.

Ding, Y., et al., Adaptive All-Order Dispersion Compensation Of Ultrafast Laser Pulses Using Dynamic Spectral Holography; American Institute of Physics, pp. 3255-3257; 1999.

Jones, R. et al.; Adaptive Femtosecond Optical Pulse Combining: American Institute of Physics, pp. 3692-3694; 2000.

Lahiri, I et al.; Photorefractice p-i-n Diode AQuantum Well Spatial Light Modulators; American Institute of Physics, pp. 1408-1738; 1995.

Nolte, D.D., Self-Adaptive Optical Hologrphy In Quantum Wells, pp. 1-6, 2005.

La Clair, J. et al.; Molecular Screening On A Compact Disc; The Royal Society of Chemistry; pp. 3244-3249; 2003.

Burkart et al. UCSD Scientists Develope Novel Way to Screen Molecules Using Conventional CDS an Compact Disk Players: UCSD newsletter; pp. 1-4, 2003.

Kwolek, K.M. et al.; Photorefractive Asymmetric Fabry-Perot Quantum Wells: Transverse-filed Geometry; Appl. Phys Lett, vol. 67, pp. 736-738, 1995.

* cited by examiner

METHOD AND APPARATUS FOR PHASE CONTRAST QUADRATURE INTERFEROMETRIC DETECTION OF AN IMMUNOASSAY

RELATED APPLICATIONS

This application claims priority to U.S. Provisional Patent Application No. 60/649,070, filed Feb. 1, 2005, entitled "Phase-Contrast Quadrature For Spinning Disk Interferometry And Immunological Assay". This application also claims priority to U.S. Provisional Patent Application No. 60/755,177, filed Dec. 30, 2005, entitled "Phase-Contrast BioCD: High-Speed Immunoassays at Sub-Picogram Detection Levels".

This application is related to U.S. application Ser. No. 10/726,772 filed Dec. 3, 2003 as well as its parent application that resulted in U.S. Pat. No. 6,685,885. This application is also related to U.S. Provisional Application No. 60/649,071, entitled "Laser Scanning Interferometric Assays" [and also U.S. application Ser. No. 11/345,564 being filed on the same day as the present application that claims priority to this provisional application and entitled "Laser Scanning Interferometric Surface Metrology"], U.S. Provisional Application No. 60/649,043, entitled "Multiplexed Laser-Scanning Interferometric Biochips and Biodisks" [and also U.S. application Ser. No. 11/345,477 being filed on the same day as the present application that claims priority to this provisional application and entitled "Multiplexed Biological Analyzer Planar Array Apparatus and Methods"], and U.S. Provisional Application No. 60/648,724, entitled "Method for Conducting Carrier-Wave Side-Band Optical Assays for Molecular Recognition" [and also U.S. application Ser. No. 11/345,566 being filed on the same day as the present application that claims priority to this provisional application and entitled "Differentially Encoded Biological Analyzer Planar Array Apparatus and Methods"], all three of these provisional applications having been filed on Feb. 1, 2005.

FIELD OF THE INVENTION

The present invention generally relates to a device for detecting the presence of specific biological material in a sample, and more particularly to a laser compact disc system for detecting the presence of biological pathogens and/or analyte molecules bound to target receptors on the disc by sensing changes in the optical characteristics of a probe beam reflected from the disc caused by the pathogens and/or analytes.

BACKGROUND OF THE INVENTION

In many chemical, biological, medical, and diagnostic applications, it is desirable to detect the presence of specific molecular structures in a sample. Many molecular structures such as cells, viruses, bacteria, toxins, peptides, DNA fragments, and antibodies are recognized by particular receptors. Biochemical technologies including gene chips, immunological chips, and DNA arrays for detecting gene expression patterns in cancer cells, exploit the interaction between these molecular structures and the receptors. [For examples see the descriptions in the following articles: Sanders, G. H. W. and A. Manz, *Chip-based microsystems for genomic and proteomic analysis*. Trends in Anal. Chem., 2000, Vol. 19(6), p. 364-378. Wang, J., *From DNA biosensors to gene chips*. Nucl. Acids Res., 2000, Vol. 28(16), p. 3011-3016; Hagman, M., *Doing immunology on a chip*. Science, 2000, Vol. 290, p. 82-83; Marx, J., *DNA Arrays reveal cancer in its many forms*. Science, 2000, Vol. 289, p. 1670-1672]. These technologies generally employ a stationary chip prepared to include the desired receptors (those which interact with the target analyte or molecular structure under test). Since the receptor areas can be quite small, chips may be produced which test for a plurality of analytes. Ideally, many thousand binding receptors are provided to provide a complete assay. When the receptors are exposed to a biological sample, only a few may bind a specific protein or pathogen. Ideally, these receptor sites are identified in as short a time as possible.

One such technology for screening for a plurality of molecular structures is the so-called immunological compact disk, which simply includes an antibody microarray. [For examples see the descriptions in the following articles: Ekins, R., F. Chu, and E. Biggart, *Development of microspot multianalyte ratiometric immunoassay using dual flourescent-labelled antibodies*. Anal. Chim. Acta, 1989, Vol. 227, p. 73-96; Ekins, R. and F. W. Chu, *Multianalyte microspot immunoassay—Microanalytical "compact Disk" of the future*. Clin. Chem., 1991, Vol. 37(11), p. 1955-1967; Ekins, R., *Ligand assays: from electrophoresis to miniaturized microarrays*. Clin. Chem., 1998, Vol. 44(9), p. 2015-2030]. Conventional fluorescence detection is employed to sense the presence in the microarray of the molecular structures under test. Other approaches to immunological assays employ traditional Mach-Zender interferometers that include waveguides and grating couplers. [For examples see the descriptions in the following articles: Gao, H., et al., *Immunosensing with photo-immobilized immunoreagents on planar optical wave guides*. Biosensors and Bioelectronics, 1995, Vol. 10, p. 317-328; Maisenholder, B., et al., *A GaAs/AlGaAs-based refractometer platform for integrated optical sensing applications*. Sensors and Actuators B, 1997, Vol. 38-39, p. 324-329; Kunz, R. E., *Miniature integrated optical modules for chemical and biochemical sensing*. Sensors and Actuators B, 1997, Vol. 38-39, p. 13-28; Dübendorfer, J. and R. E. Kunz, *Reference pads for miniature integrated optical sensors*. Sensors and Actuators B, 1997 Vol. 38-39, p. 116-121; Brecht, A. and G. Gauglitz, *recent developments in optical transducers for chemical or biochemical applications*. Sensors and Actuators B, 1997, Vol. 38-39, p. 1-7]. Interferometric optical biosensors have the intrinsic advantage of interferometric sensitivity, but are often characterized by large surface areas per element, long interaction lengths, or complicated resonance structures. They also can be susceptible to phase drift from thermal and mechanical effects.

While the abovementioned techniques have proven useful for producing and reading assay information within the chemical, biological, medical and diagnostic application industries, developing improved fabrication and reading techniques for planar arrays with significant improvement in performance over existing planar arrays technology is desirable.

SUMMARY OF THE INVENTION

In one aspect of the invention there is a label-free phase-contrast quadrature inteferometric method of detecting the presence or absence of a target analyte in a biological sample. The method comprising exposing a reflecting surface of a substrate to the biological sample. The reflecting surface has a spatial pattern of coatings of receptor molecules. Each coating is specific to a particular target analyte. The method further comprises using a split-photodetector to measure intensity in a far-field diffraction pattern of a reflected signal. The reflected signal results from a focused probe laser beam having a wavelength λ that is incident with waist $w_o$ on the spatial pattern of coatings of receptor molecules. The reflected signal also resulting from scanning at least a portion of the substrate. The method further comprises measuring intensity of a portion of the reflected signal in a substantially quadrature condition by measuring intensity with the split-photodetector of at least one of two observation angles. The two observation angles being substantially equal to a pair of quadrature angles. The quadrature angles $\Theta_q$ are defined from a ray normal to the substrate by a formula: $\Theta_q = \sin^{-1}(\lambda/2w_o)$.

In one variation on an aspect of the invention the intensity measurement of the far-field diffraction pattern of the reflected beam is done in a Fourier plane.

In another variation on an aspect of the invention the method further comprises inverting an output of the split-photodetector at one of the pair of quadrature angles and summing the inverted output with an output of the split-photodetector at the other of the pair of quadrature angles.

In another variation on an aspect of the invention the method further comprises passing the reflected signal through an objective lens prior to measuring intensity using the split-photodetector.

In another variation on an aspect of the invention the substrate is a disk and scanning of the substrate is done by rotating the disk.

In another aspect of the invention there is a quadrature interferometric method for determining the presence or absence of a target analyte in a sample. The method comprises using a laser beam having a wavelength λ and a waist $w_o$ to probe at least a portion of a substrate. The portion of the substrate having a reflecting surface that has been exposed to the sample. The reflecting surface includes at least a first region having a layer of recognition molecules specific to the target analyte and a second region that does not include a layer of recognition molecules specific to the target analyte. The method further comprises measuring a time dependent intensity on a photodetector of a substantially only first quadrature at one of a pair of quadrature angles $\Theta_q$ of a reflected diffraction signal of the probe beam while probing the first region and the second region.

In one variation on an aspect of the invention the time dependence arises from a relative motion of the incident laser beam with respect to the substrate.

In another variation on an aspect of the invention the substrate is a disk and the relative motion of the disk with respect to the incident laser beam is generated by rotating the disk.

In another variation on an aspect of the invention the reflected diffraction signal of the laser beam is measured using a split-photodetector configuration. The method further comprising inverting a first output portion of the reflected signal corresponding to the one of the pair of quadrature angles. The inverted first output being summed with a second output of the reflected signal corresponding to the other of the pair of quadrature angles.

In another variation on an aspect of the invention the substrate is a disk and the reflected diffraction signal is passed through an objective lens prior to measuring the intensity.

In another variation on an aspect of the invention the method further comprises passing the reflected diffraction signal of the probe beam through a π/2 phase mask prior to measuring the intensity.

In another variation on an aspect of the invention the reflecting surface is substantially flat. The quadrature angles are defined from a ray normal to the substrate by a formula: $\Theta_q = \sin^{-1}(\lambda/2w_o)$.

In another variation on an aspect of the invention the substrate is a disk and the reflecting surface of the disk includes a plurality of lands and a plurality of ridges. The ridges have a height h. The quadrature angles are defined from a ray normal to the substrate by a formula: $\Theta_q = \sin^{-1}[(\lambda/2 - 4h)/w_o]$.

In another aspect of the invention there is a phase-contrast quadrature interferometric step-detection method of determining the presence or absence of a target analyte in a sample. The method comprises measuring time dependent intensity of a far-field diffraction pattern of a reflected light signal resulting from a probe laser beam incident on a disk having a spatial pattern of recognition molecules using a split photodetector configuration. The method further comprises summing contributions from a first quadrature and a second opposing quadrature of the resulting light signal. The summing of the contributions is preceded by inversion of the contribution of the first quadrature.

In one variation on an aspect of the invention the intensity is measured of the resulting light signal that is reflected from a reflecting surface of the disk.

In another variation on an aspect of the invention the split photodetector configuration is a split-ring photodetector.

In another variation on an aspect of the invention the split photodetector configuration is a quadrant photodetector.

In another variation on an aspect of the invention the split photodetector configuration includes a first and a second photodetector. The probe beam has a wavelength λ and a waist $w_o$ incident on the disk. The first and second photodetectors measure intensity at substantially a pair of quadrature angles $\Theta_q$. The quadrature angles are defined from a ray normal to the disk by a formula $\Theta_q = \sin^{-1}(\lambda/2w_o)$.

In another variation on an aspect of the invention time dependent intensity is measured by rotating the disk.

In another variation on an aspect of the invention the disk is rotating at about 80 Hz.

In another aspect of the invention there is a phase-contrast quadrature interferometric step-detection method of determining the presence or absence of a target analyte in a sample. The method comprises measuring a time dependent difference at substantially a first quadrature interference angle of a first portion of a reflected light signal of a substantially only first quadrature. The reflected light signal results from tracing a laser beam across alternating regions of a specific antibody and a non-specific antibody on a planar array.

In one variation on an aspect of the invention the method further comprises measuring a time dependent difference at substantially a second quadrature interference angle of a second portion of the reflected light signal of a substantially only second quadrature resulting from the tracing of the laser beam across alternating regions of the planar array.

In another variation on an aspect of the invention the method further comprises inverting a first output of the first portion of the reflected light signal. The method also comprises summing the inverted first output with a second output of the second portion of the reflected light signal.

In another aspect of the invention there is a scale free label free quadrature interferometric step-detection method of determining the presence or absence of a target analyte in a sample. The method comprises using a focused laser beam having an incident waist $w_o$ and a wavelength λ to scan a disk. The disk has a spatially patterned layer of receptor molecules specific to the target analyte. The layer has a substantially sharp layer edge. The method further comprises detecting intensity change in a far-field diffraction pattern caused by scanning the substantially sharp layer edge using a split photodetector configuration. The split photodetector configuration provides an output of the far-field diffraction pattern at substantially at least one of a pair of quadrature interference angles defined from a ray normal to the disk.

In another aspect of the invention there is a quadrature interferometric method of determining the presence or absence of a target analyte in a sample. The method comprises measuring an output of a first photodetector aligned in an optical train to receive a substantially only first quadrature of a reflected light signal. The substantially only first quadrature results from observing at substantially a first quadrature angle the reflected light signal. The reflected light signal results from a probe laser beam having a wavelength $\lambda$ and a waist $w_o$ incident on a planar array. The planar array has at least one ridge defined by a layer of receptor molecules specific to the target analyte. The quadrature angles $\Theta_q$ are defined from a ray normal to the planar array by a formula:

$$\Theta_q = \sin^{-1}(\lambda/2w_o).$$

In one variation on an aspect of the invention the method further comprises measuring an output of a second photodetector aligned in the optical train to receive a substantially only second opposing quadrature resulting from observing at substantially a second quadrature angle the reflected light signal.

In another variation on an aspect of the invention the first and second photodetectors are measuring the far-field diffraction pattern of the reflected light signal in a Fourier plane.

In another variation on an aspect of the invention the method further comprises inverting the output of the first photodetector, and summing the inverted output of the first photodetector with the output of the second photodetector.

In another variation on an aspect of the invention the optical train includes an objective lens.

In yet another aspect of the invention there is a kit for interferometric detection of the presence or absence of a target analyte in a biological sample. The kit comprises an optical source for a focused laser beam of wavelength $\lambda$ with waist $w_o$. The optical source is aligned to directly or indirectly make the laser beam incident on a substrate. The substrate has a reflecting surface with a spatially-patterned biolayer. The biolayer includes a plurality of coatings of receptor molecules, each coating configured to bind a particular target analyte. The kit further comprises a split photodetector for measuring intensity of a far-field diffraction pattern. The split photodetector is positioned to detect intensity substantially only at an observation angle substantially equal to at least one of a pair of quadrature angles. The quadrature angles are defined from a ray normal to the substrate by the formula:
$\Theta_q = \sin^{-1}(\lambda/2w_o).$ In one variation on an aspect of the invention the split photodetector includes an aperture for blocking portions of the far-field diffraction pattern except at the qudrature angles.

In another variation on an aspect of the invention the reflecting surface comprises a 10-layer dielectric stack of $Ti_2O_5/SiO_2$ that serves as a laser mirror.

In another variation on an aspect of the invention the split photodetector is a quadrant photodetector, and the reflecting surface comprises a quarter-wave dielectric stack.

In yet another aspect of the invention there is an apparatus for phase-contrast quadrature interferometric detection of the presence or absence of a target molecule on a planar array. The apparatus comprises a laser source for generating a probe beam. The apparatus also comprising a platform for receiving the planar array. The apparatus further comprising a first optical train for directing the probe beam at the platform in a substantially surface normal manner. The apparatus also comprising an objective lens having a first side and a second side and having a focal length. The objective lens being offset on the first side of the lens from the platform by a first distance approximately equal to the focal length. The apparatus further comprising a split photodetector means for measuring a first quadrature and a second quadrature in a signal resulting from reflection of the probe beam.

In one variation on an aspect of the invention the planar array is a disk. The apparatus further includes a spinner attached to the platform for rotating the disk.

In another variation on an aspect of the invention the split photodetector means for measuring is a quadrant photodetector positioned to produce a first output for the first quadrature in the signal and a second output for the second quadrature in the signal.

In another variation on an aspect of the invention the apparatus further comprises an inversion circuit attached to one of the first output and the second output and a summing circuit attached to the inversion circuit and to the other of the first output and the second output.

In another variation on an aspect of the invention the split photodetector means for measuring is a first photodetector positioned to produce a first output for the first quadrature in the signal and a second photodetector positioned to produce a second output for the second quadrature in the signal.

In another variation on an aspect of the invention the split photodetector means for measuring is a split-ring photodetector positioned to produce a first output for the first quadrature in the signal and a second output for the second quadrature in the signal.

In another variation on an aspect of the invention the means for measuring is offset from the second side of the objective lens by a second distance approximately equal to the focal length.

In yet another aspect of the invention there is a system for phase contrast quadrature interferometric detection of the presence or absence of a target analyte in a sample exposed on a disk having a reflecting surface including a plurality of spatially patterned coatings of recognition molecules, at least one recognition molecule being specific to the target analyte. The apparatus comprises a platform for receiving the disk and a spinner for rotating the disk. The apparatus also comprises an optical source for a focused laser beam of wavelength $\lambda$. The optical source is aligned to directly or indirectly make the laser beam incident with waist $w_o$ on the disk. The apparatus further comprises means for tracing the laser beam across the plurality of spatially patterned coatings of recognition molecules. The apparatus also comprises split photodetector means for measuring intensity at substantially a pair of quadrature interference angles $\Theta_q$ of a far field diffraction pattern. The far field diffraction pattern results from tracing the laser beam across the planar array. The quadrature interference angles $\Theta_q$ being defined by the formula $\Theta_q = \sin^{-1}(\lambda/2w_o).$ In one variation on an aspect of the invention the system further comprises an objective lens positioned between the disk on the platform and the split photodetector means for measuring intensity.

In another variation on an aspect of the invention the split photodetector means for measuring intensity has a first output corresponding to the intensity at one of the pair of quadrature interference angles $\Theta_q$ and a second output corresponding to the intensity at the other of the pair of quadrature interference angles $\Theta_q$.

In another variation on an aspect of the invention the system further comprises an inversion circuit attached to one of the first output and the second output and a summing circuit attached to the inversion circuit and to the other of the first output and the second output.

In another variation on an aspect of the invention the split photodetector means for measuring is a quadrant photodetector.

DETAILED DESCRIPTION

Figure 1:
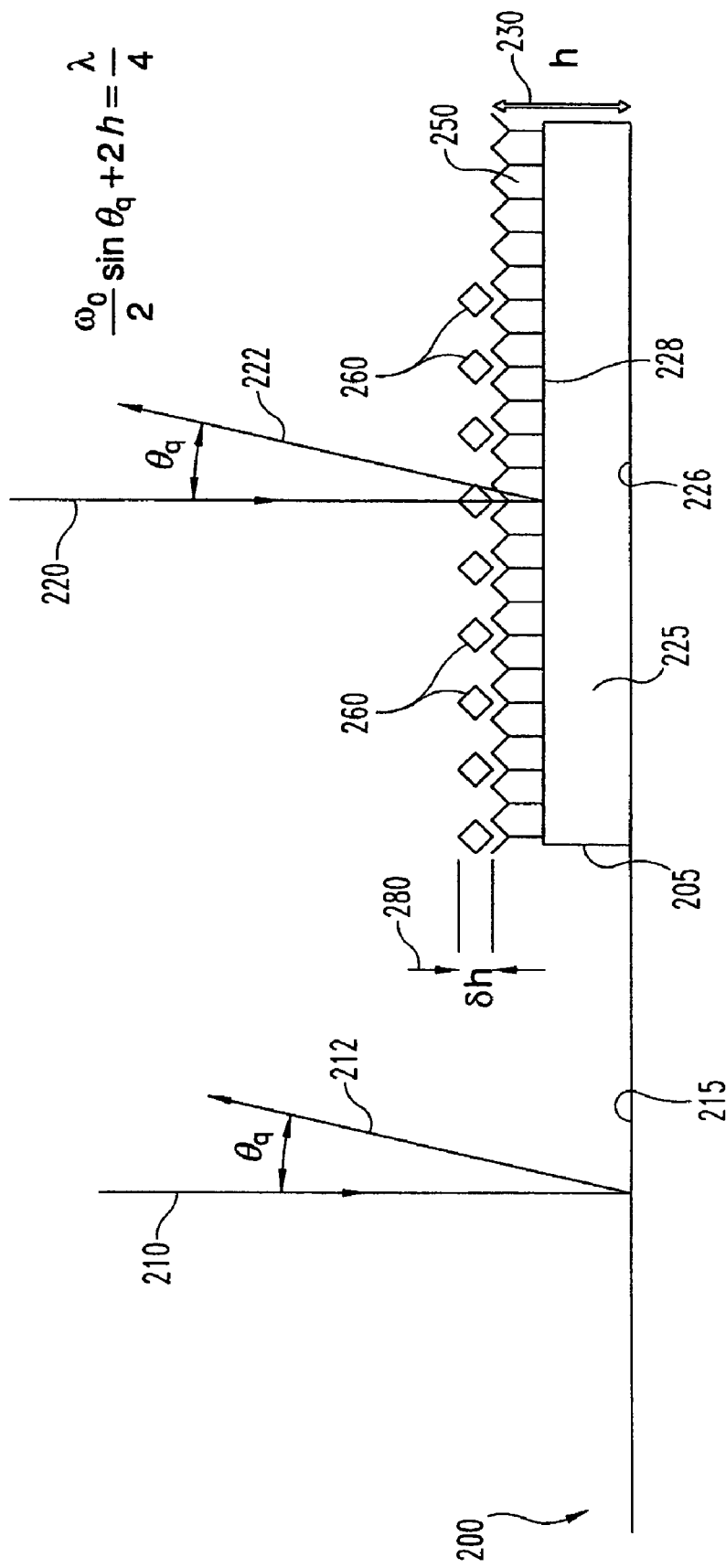
FIG. 1 illustrates one aspect of the present invention relating to a quadrature condition between a ray incident on one side of the step relative to a ray on the other side of the step for a substrate having ridges and lands.

Approaches in addition to those described in the background section are being or have been developed. Some other approaches utilize a biological, optical compact disk ("bio-optical CD" or "bioCD") system including a CD player for scanning biological CDs, which permit the use of an interferometric detection technique to sense the presence of particular analytes in a biological sample. As will be discussed further below, such bioCD devices are preferably used with an intereferometric detection system that operates substantially in a quadrature condition.

The increasing complexity of proteomics [see E. F. Petricoin, K. C. Zoon, E. C. Kohn, J. C. Barrett, and L. A. Liotta, "Clinical proteomics: Translating benchside promise into bedside reality," *Nature Reviews Drug Discovery*, vol. 1, pp. 683-695, 2002] and protein interaction networks [see P. Bork, L. J. Jensen, C. von Mering, A. K. Ramani, I. Lee, and E. M. Marcotte, "Protein interaction networks from yeast to human," *Current Opinion In Structural Biology*, vol. 14, pp. 292-299, 2004; S.-H. Yook, Z. N. Oltvai, and A.-L. Barabasi, "Functional and topological characterization of protein interaction networks," *Proteomics*, vol. 4, pp. 828-942, 2004] creates a need for biochips that can test rapidly for multi-analyte molecular recognition. An important example are protein microarrays for expression studies [see P. F. Predki, "Functional protein microarrays: ripe for discovery," *Current Opinion In Chemical Biology*, vol. 8, pp. 8-13, 2004; B. Schweitzer, P. Predki, and M. Snyder, "Microarrays to characterize protein interactions on a whole-proteome scale," *Proteomics*, vol. 3, pp. 2190-2199, 2003] and antibody chips for diagnostic medicine [see S. P. Lal, R. I. Christopherson, and C. G. dos Remedios, "Antibody arrays: an embryonic but rapidly growing technology," *Drug Discovery Today*, vol. 7, pp. S143-S149, 2002; Y. P. Ding, L. Y. Chen, W. Zhang, H. J. Cao, S. M. Ni, M. F. Zhou, H. Liang, Z. G. Ling, Y. Y. Geng, and S. Q. Wang, "Studies on simultaneously detecting multiple antibodies in the serum using microarray," *Progress in Biochemistry and Biophysics*, vol. 29, pp. 640-644, 2002; W. Kusnezow and J. D. Hoheisel, "Antibody Microarrays: Promises and Problems," *Biotechniques*, vol. 33, pp. S14-S23, 2002]. Interferometry has the advantage of higher photon fluxes than conventional fluorescence detection and consequently permits shorter detection times and/or increased signal-to-noise ratios.

One or more of the present inventors introduced the biological compact disc as a sensitive spinning-disk interferometer that operates at high-speed and is self-referencing [see M. M. Varma, H. D. Inerowicz, F. E. Regnier, and D. D. Nolte, "High-speed label-free detection by spinning-disk micro-interferometry," *Biosensors & Bioelectronics*, vol. 19, pp. 1371-1376, 2004]. Self-referencing is preferable in performing stable interferometry on a mechanically spinning disk. In order to be sensitive to optical path length, the relative phase between the signal and reference beams is locked to substantially quadrature ($\pi/2$ phase difference), preferably independent of mechanical vibrations or motion. One or more of the present inventors previously defined two quadrature interferometric detection classes of BioCD. The micro-diffraction class ("MD-class" [see M. M. Varma, D. D. Nolte, H. D. Inerowicz, and F. E. Regnier, "Spinning-disk self-referencing interferometry of antigen-antibody recognition," *Optics Letters*, vol. 29, pp. 950-952, 2004. Also see U.S. Pat. No. 6,685,885 to Nolte et al] and the adaptive optical class ("AO-class") [see U.S. patent application Ser. No. 10/726,772 filed Dec. 3, 2003 entitled "Adaptive Interferometric Multi-Analyte High-Speed Biosensor", which is incorporated by reference herein in its entirety].

The MD-class BioCD locks to quadrature using microstructures fabricated on the disk that diffract a focused laser beam to the far field with a fixed relative phase. In one embodiment, gold spokes, preferably 1024 to a disk, that have a height of $\lambda/8$ are deposited by evaporation onto a reflecting surface, and bio-molecules are immobilized on either the gold spokes or the land. Because the phase difference is set by the height difference of the local microstructure, it is unaffected by mechanical motion or vibration. Immobilized bio-molecules change the relative phase which is converted to amplitude modulation in the far field.

The AO-class locks to quadrature using self-adaptive nonlinear optical mixing, preferably in a photorefractive quantum well [see D. D. Nolte, "Semi-insulating semiconductor heterostructures: Optoelectronic properties and applications," *J. Appl. Phys.*, vol. 85, pp. 6259, 1999; D. D. Nolte and M. R. Melloch, "Photorefractive Quantum Wells and Thin Films," in *Photorefractive Effects and Materials*, D. D. Nolte, Ed. Dordrecht: Kluwer Academic Publishers, 1995] that adaptively tracks the phase between the signal and the reference [see D. D. Nolte, T. Cubel, L. J. Pyrak-Nolte, and M. R. Melloch, "Adaptive Beam Combining and Interferometry using Photorefractive Quantum Wells," *J. Opt. Soc. Am. B*, vol. 18, pp. 195-205, 2001]. In one embodiment, patterned protein structures modulate optical phase of the probe beam, which is sent to a photorefractive quantum well (PRQW) device and mixed with a reference local oscillator beam by two-wave mixing. The two-wave mixing self-compensates mechanical disturbances to maintain the quadrature condition with a compensation rate higher than a kHz. Phase modulation caused by protein structures on the spinning disk have frequencies higher than the compensation rate and is read out by photodetector.

These BioCD quadrature classes traded off complexity between the near-field and the far-field. MD-class BioCDs appear to require more complex microstructuring on the disk, while AO-class disks required holographic films for the nonlinear optical mixing. The present invention introduces a new quadrature class analogous to phase-contrast imaging. For this reason, various embodiments of the present invention will often be referred to herein as the Phase-Contrast class ("PC-class").

Prior to describing various embodiments of the PC-class the intended meaning of quadrature in the interferometric detection system(s) of the present invention is further explained. In some specific applications quadrature might be narrowly construed as what occurs in an interferometric system when a common optical "mode" is split into at least 2 "scattered" modes that differ in phase about $N*\pi/2$ (N being an odd integer). However, as used in the present invention (and the previously referred to issued patents and/or pending applications of Nolte et al.) an interferometric system is in quadrature when at least one mode "interacts" with a target molecule and at least one of the other modes does not, where these modes differ in phase by about $N*\pi/2$ (N being an odd integer). This definition of quadrature is also applicable to interferometric systems in which the "other mode(s)" interact with a different molecule. The interferometric system may be considered to be substantially in the quadrature condition if the phase difference is $\pi/2$ (or $N*\pi/2$, wherein N is an odd integer) plus or minus approximately twenty percent.

Additionally, prior to describing various embodiments of the PC-class the intended meaning of "edge" or "edge-detection" in the quadrature interferometric detection of the present invention is further explained. Various portions of the description of one or more embodiments below might refer to an edge that diffracts light. It will be understood by those of ordinary skill in the art that the description for all embodiments disclosed herein of a step or an edge diffracting light in reality refers to the fact that light diffraction is integrated over the full optical wavefront. Strictly speaking it is not just the edge that diffracts light. It is the discontinuity or step that is integrated over the beam that diffracts to the far field and is detected. The discontinuity of the step of the differing heights places different conditions on the wave to the left and right. It is the integrated difference that is detected as diffraction, and not just a step or an edge. Moreover, with respect to the present application the term "edge" or "edge-detection" is intended to encompass generally the differential detection techniques disclosed herein. That is to say, quadrature interferometric detection that detects the slope or derivative of the surface height. The signal is proportional to dh(x)/dx. While more common usage of the term might indicate that only in the special case of a discontinuous step is something an "edge-detection" process, the terms as used herein are intended to be defined more broadly as set forth in this paragraph to also encompass "slope detection" across a step.

The present invention generally relates to the improved fabrication and reading of spinning-disk immunoassays (Bio-CDs). In one embodiment a phase contrast quadrature interferometric condition is preferably established for the disk. The system preferably has light detection efficiency up to 100%. The system also preferably has automatic compensation of laser intensity drift.

Various embodiments of the present invention generally relate to a method for converting a spatial optical phase variation in a material into a time-dependent intensity using the quadrature condition between a signal and a reference wave in which the quadrature condition is established by diffraction from an index variation. The optical phase variation can be intrinsic refractive index variations to a substrate material, or arising from material added to the substrate as for immobilized proteins or nucleic acids. To detect the phase modulation, Fourier filtering can be used comprised of phase masks, amplitude masks, or both phase and amplitude masks. The masks can be centered in the Fourier plane or oblique. This signal is detected with a photodetector either in whole or in part, with detector apertures, or with split-detector configurations to sum contributions from opposite quadratures. The time dependence arises from a relative motion of the probe laser spot with respect to the material, or vice versa.

As will be discussed below, one or more embodiments of the present invention include an optical train employing one or more lenses. In any optical system employing lenses, there are special planes defined. These include the object plane (where the object resides), the lens plane (where the lens resides) and an image plane (where the image resides) and detector planes (where the light is detected). With multiple lenses there may be multiple image planes. In special optical systems when the object plane is one focal length from the lens plane, a Fourier plane is defined at a location of one focal length on the opposite of the lens to the object plane. Apertures and masks can be placed at Fourier planes or images planes or at lens planes (immediately before or behind the lenses) or detector planes. These apertures and masks can control the amount of transmitted light (amplitude mask) or the light phase (phase masks). The purpose of the masks at the different planes is to produce the strongest constructive interference, and hence signal, at the detector. A widely varying set of parameters in the selection of possible mask patterns and locations that control the intensity detected by a single detector or a detector array are contemplated as within the scope of the invention. Signals are thereby optimized and maximized by appropriate choice of masks and locations.

It should be understood that a wide variety of split detector configurations and other means for measuring intensity of the reflected light signal (including, but not limited to, the far-field diffraction pattern) of at least one and possibly both (opposing) quadrature conditions of the reflected light signal at the two quadrature angles. All such split detector configurations or means for measuring are contemplated as within the scope of the present invention. In one embodiment, the split-detector configuration might be a split-ring photodetector. As will be discussed further below, in one embodiment a split-photodetector is used in conjunction with inversion and summing circuits. Alternatively, two separate photodetectors might be used, each positioned to receive the signal of opposite quadrature. In these and other variations described herein it should be understood that the means for measuring intensity may be part of a larger optical train that might include apertures, various phase and/or amplitude marks, and other components known to those of ordinary skill in the art. Another possible variation uses a single photodetector in which the signal encounters an aperture and/or a knife edge that shields at least a portion of the photodetector so that the photodetector receives a signal that contains substantially a single quadrature. The split detector configuration might also be a quadrant photodetector. Other variations known to those of ordinary skill in the art are contemplated as within the scope of the invention. For example, it should be noted that a split detector or a quadrant detector are just specific cases of detector arrays that can grow quite large, with many numbers of detector elements.

In at least some embodiments of the present invention the role of the phase mask in the optical system is replaced by a split photodetector with a differenced electronic output. The implementation in such embodiments might be considered at least partially advantageous in both the near-field and the far-field. In the near-field (as compared to the MD-class) microstructuring of the disk is preferably not required. In the far-field (as compared to the AO-class) a less complex detection might preferably be used. The approach is preferably still self-referencing (providing at least some stability against mechanical motion). Also, various embodiments of the present invention lock to quadrature through step diffraction off, for example, spatially varying immobilized protein patterns on the disk.

With references to FIGS. 1-4 there will now be explained some of the aspects of one or more embodiments of the present invention relating to step-diffraction quadrature. FIG. 1 illustrates one aspect of at least some embodiments of the present invention that make use of step diffraction and the quadrature angle.

Referring to FIG. 1, in one embodiment of the present invention substrate 200 preferably has a plurality of lands 215 and ridges 225 with an edge 205 at the interface between the land 215 and ridge 225. Ray 210 is incident on land 215 and ray 220 is incident on ridge 225. Ridge 225 has a height h (reference numeral 230 in FIG. 1) defined by ridge 225 that includes the thickness between bottom surface 226 and top surface 228 as well as the added thickness of layer of receptor molecules 250. Height differential δh is caused by the added thickness of target molecules 260 (examples of target analytes/molecules include, but are not limited to, proteins) that bind to receptor molecules 250. It should be understood that other embodiments are contemplated as within the scope of the invention, such as embodiments wherein the receptor molecules 250 are not bound directly to lands 215 or ridges 225 of the reflective substrate 200, but instead to some intermediate layer.

As shown in FIG. 1, edge 205 diffracts light and establishes a quadrature condition between ray 210 incident on one side of the step relative to a ray 220 on the other side of the step. For example, for a protein or other target analyte immobilized at a height 230 (referred to as height h in the equations that follow), the quadrature angle $\Theta_q$ is given by:

$$0.5 * w_o * \sin \Theta_q + 2h = \lambda/4$$

for an incident laser beam having a wavelength $\lambda$ and a beam width $w_o$. Thus, $$\Theta_q = \arcsin [(\lambda/2 - 4h)/w_o]$$

At the quadrature angle $\Theta_q$, the reflected ray 222 from the ridge and the reflected ray 212 from the land have a relative phase difference of π/2, or quadrature. In the far field, the intensity at the quadrature angle $\Theta_q$ is equal to one half. The intensity at the quadrature angle $\Theta_q$ will be linearly sensitive to the presence of target molecules 260, (including but not limited to, proteins or other biological molecules) on the ridge 225. It will be understood by those of skill in the art that an alternative equivalent description is that the discontinuous change in optical phase causes the reflected beam to shift laterally on the detector, or an angular deflection.

Figure 2:
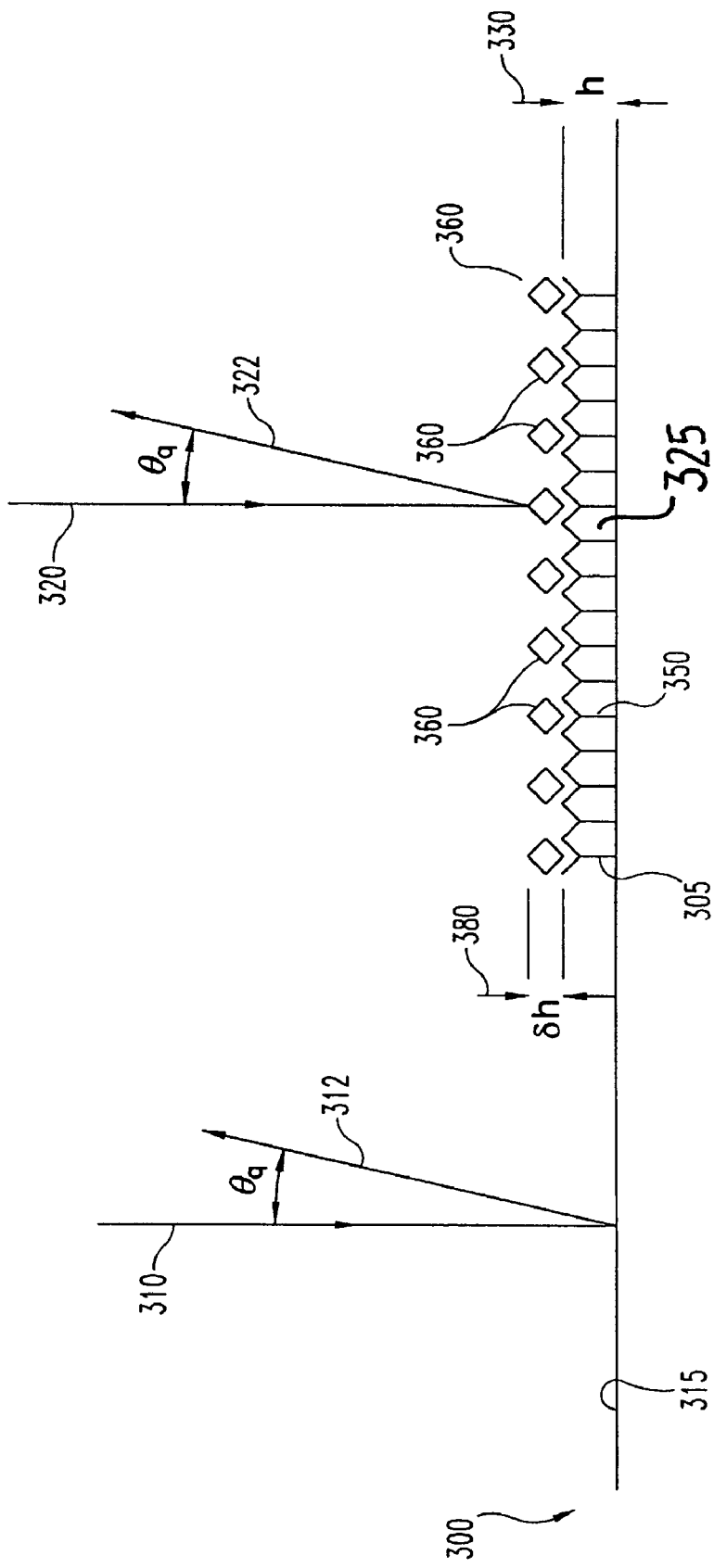
FIG. 2 illustrates an embodiment similar to FIG. 1 in which the height of the "ridge" is as small as the thickness of a biolayer.

Referring to FIG. 2, it should be understood that the "ridge" can have a height h (reference numeral 330 in FIG. 2) set by the receptor layer 350 itself (in other words the height h is as small as the thickness of a biolayer or receptor molecules 350). In this embodiment of the present invention substrate 300 preferably has a plurality of lands 315 and ridges 325 with an edge 305 at the interface between the land 315 and ridge 325. Ray 310 is incident on land 315 and ray 320 is incident on ridge 325. Ridge 325 has a height h (reference numeral 330 in FIG. 2) defined by the thickness of layer of receptor molecules 350. Height differential δh is caused by the added thickness of target molecules 360 (examples of target analytes/molecules include, but are not limited to, proteins) that preferably bind to receptor molecules 350.

As shown in FIG. 2, edge 305 diffracts light and establishes a quadrature condition between ray 310 incident on one side of the edge relative to a ray 320 on the other side of the edge. For example, for a protein or other target analyte immobilized at a height 330 (referred to as height h in the equations that follow), the quadrature angle $\Theta_q$ is given by:

$$0.5 * w_o * \sin \Theta_q = \lambda/4$$

for an incident laser beam having a wavelength $\lambda$ and a beam width $w_o$. Thus, $$\Theta_q = \arcsin [\lambda/(2 * w_o)]$$

Again, there is linear sensitivity to the biological molecules at the quadrature angle, $\Theta_q$, as illustrated in FIG. 2.

Figure 3A:
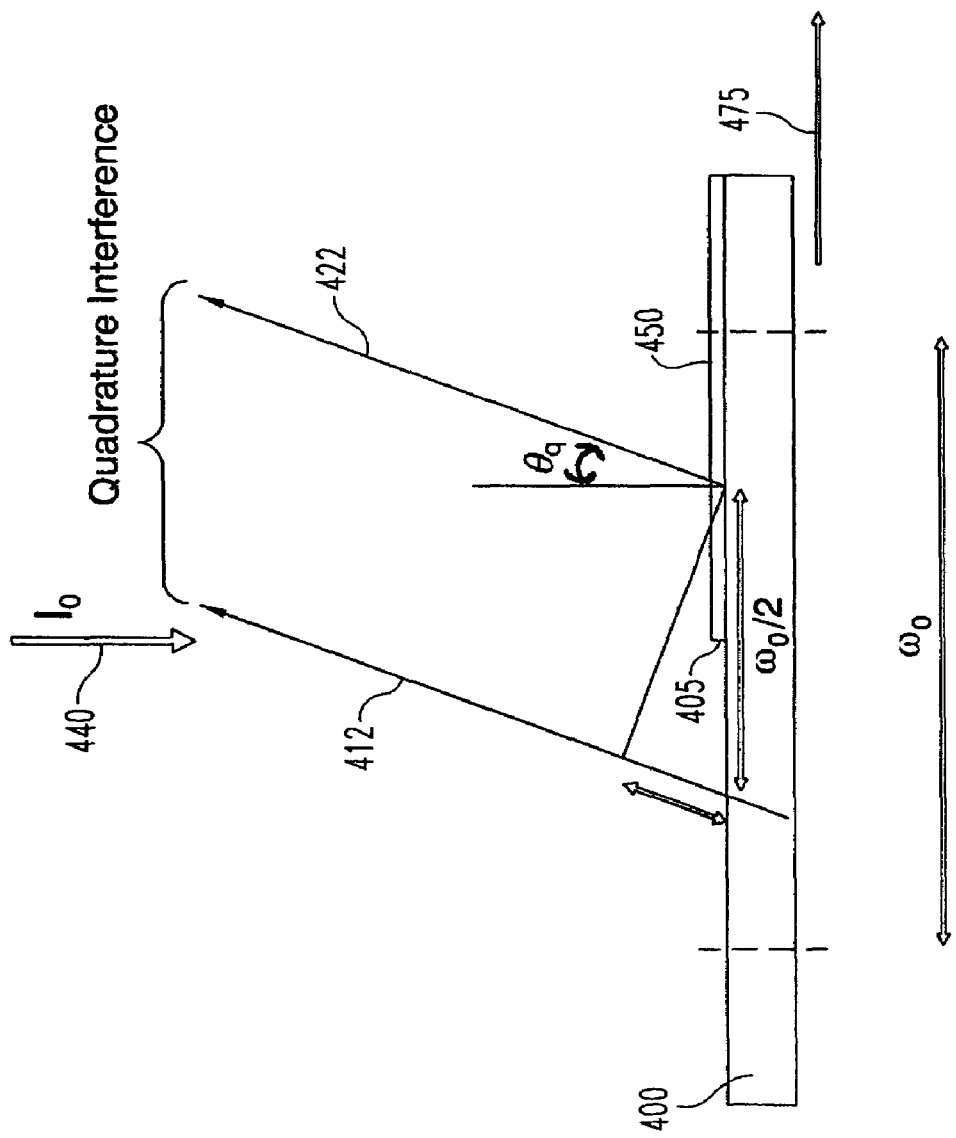
FIG. 3A illustrates step-detection establishing quadrature in the diffracted far field.
Figure 3B:
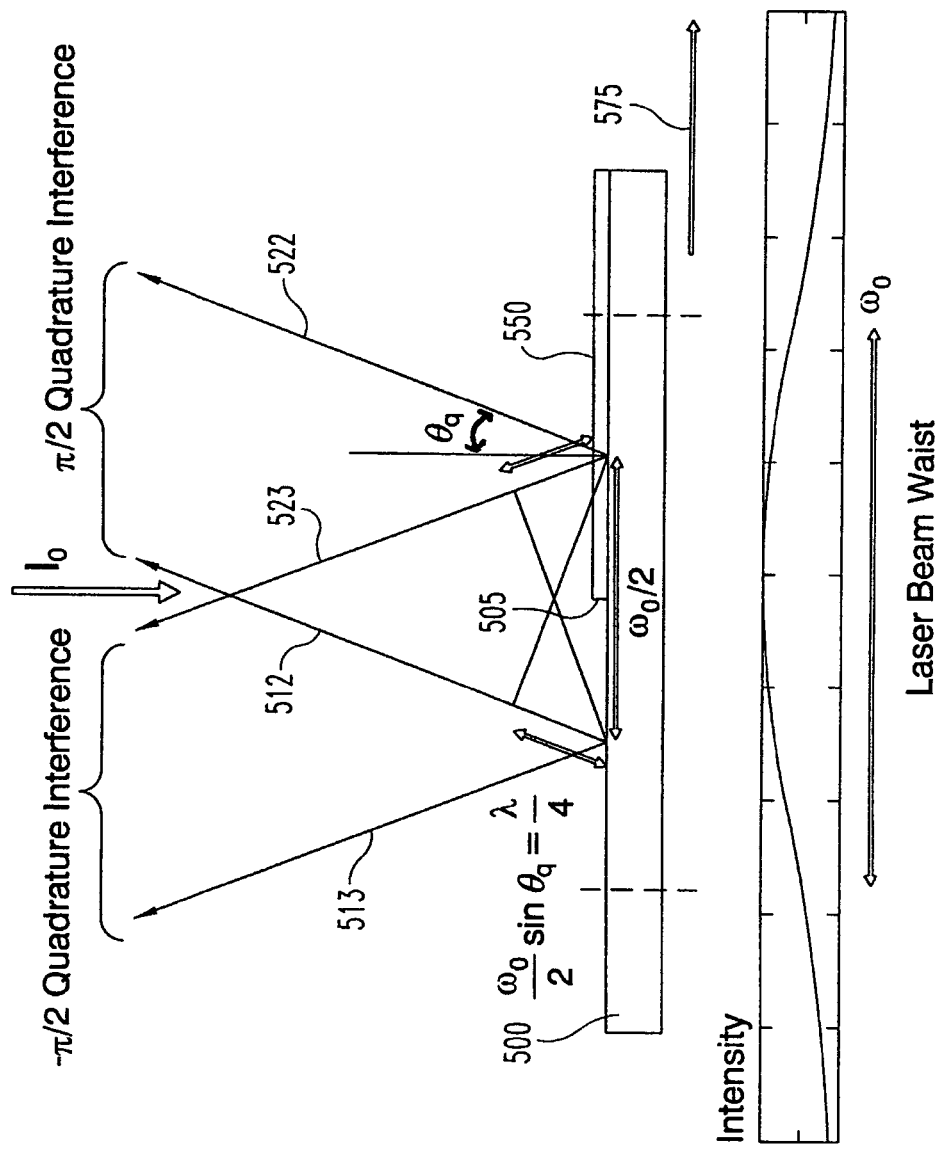
FIG. 3B is a schematic drawing of a laser beam focused onto a protein step and the intensity distribution of the incident laser beam waist. At the two quadrature angles, a phase shift ($+\pi/2$ or $-\pi/2$) caused by the protein layer establishes quadrature in the diffracted far field light intensity.

If the protein is printed as a spoke pattern, or as rectangular array elements, then when the printed protein sweeps through a finite width laser spot, quadrature occurs at a well-defined angle that depends only on the laser spot size and is substantially independent of the protein receptor layer thickness. With reference to FIGS. 3A and 3B there are illustrated aspects of step (or slope) detection phase-contrast detection establishing quadrature in the diffracted far field. In general terms, when the step is illuminated by a finite beam size, the part of the scattered wave from the protein and from the bare substrate (or alternate protein) will be in phase quadrature at a quadrature angle set by $\Theta_q$ when there is a π/2 phase difference between the partial waves.

FIG. 3A shows a finite beam 440 having intensity $I_0$, wavelength $\lambda$, and width $w_o$ illuminating the edge 405 of printed protein 450 (preferably a pattern of printed protein) atop reflective substrate 400. Motion of the substrate 400 (preferably a spinning disk) is indicated by arrow 475. The reflected rays 412 and 422 are traced from the mid-points of each half of the beam. At a specific angle, the quadrature angle $\Theta_q$, the rays have a relative π/2 phase shift. The quadrature angle $\Theta_q$ is $$\Theta_q = \arcsin [\lambda/(2 * w_o)]$$

With reference to FIG. 3B, it will be understood that there are two angles at which the reflected rays are in the quadrature condition. That is to say, there are two quadratures, one for $+\Theta_q$ and one for $-\Theta_q$. FIG. 3B shows a finite beam 540 having intensity $I_0$, wavelength $\lambda$, and width $w_o$ illuminating the edge 505 of printed protein 550 (preferably part of a pattern of printed protein) atop reflective substrate 500. The bottom portion of FIG. 3B illustrates the (Gaussian) drop off in intensity across the width $w_o$ of the beam waist. Motion of the substrate 500 (preferably a spinning disk) is indicated by arrow 575. The reflected rays 512 and 522 are traced from the mid-points of each half of the beam and trace the $+\Theta_q$ quadrature angle, wherein the rays have a relative $\pi/2$ phase shift and quadrature interference. The reflected rays 513 and 523 are traced from the mid-points of each half of the beam and trace the $-\Theta_q$ quadrature angle, wherein the rays have a relative phase shift of $-\pi/2$ and quadrature interference.

Figure 4:
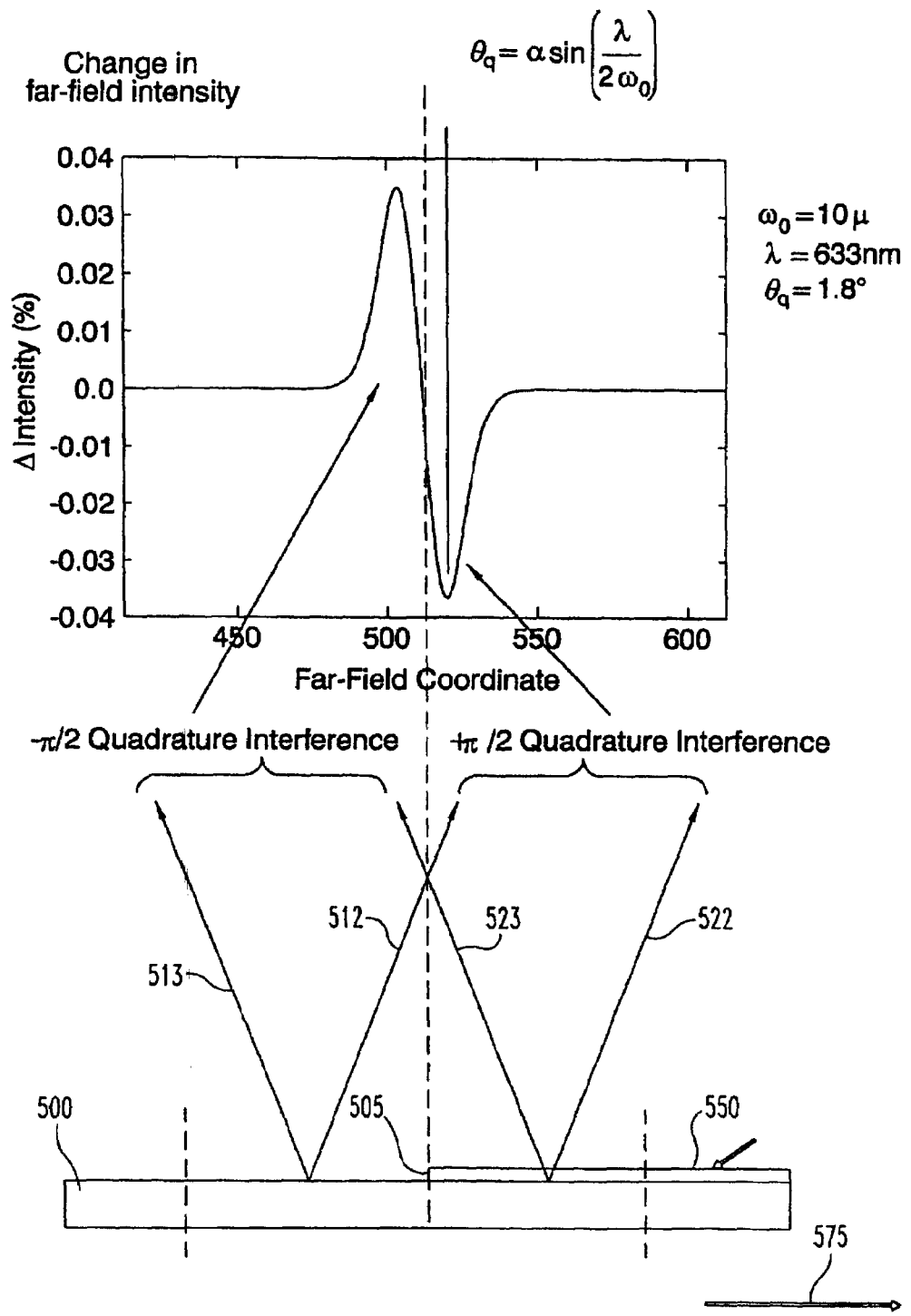
FIG. 4 illustrates one aspect of the present invention in which a diffracting protein step has dual quadratures in the far field.

Referring now to FIG. 4 it should be understood that like elements are labeled with the same reference numerals as previously used. The change in intensity in the far field is plotted in the upper portion of FIG. 4 showing an increase on one half of the beam and a decrease on the other. As previously mentioned, a diffracting protein step has dual quadratures in the far field. One leads to positive change in intensity, the other negative. During detection, one or the other is preferably detected. Alternatively, both are detected but the phase of one is flipped before both are added together. Thus, if the full field is detected, these two quadratures would cancel in the absence of inversion of one quadrature signal. However, if half of the far field is collected with, for example, a knife-edge, then half the possible signal is extracted. Moreover, if a split-detector configuration is used with an inverter and summation circuit, then a full signal can be obtained, as discussed below with respect to FIGS. 5A and 5B.

Figure 5A:
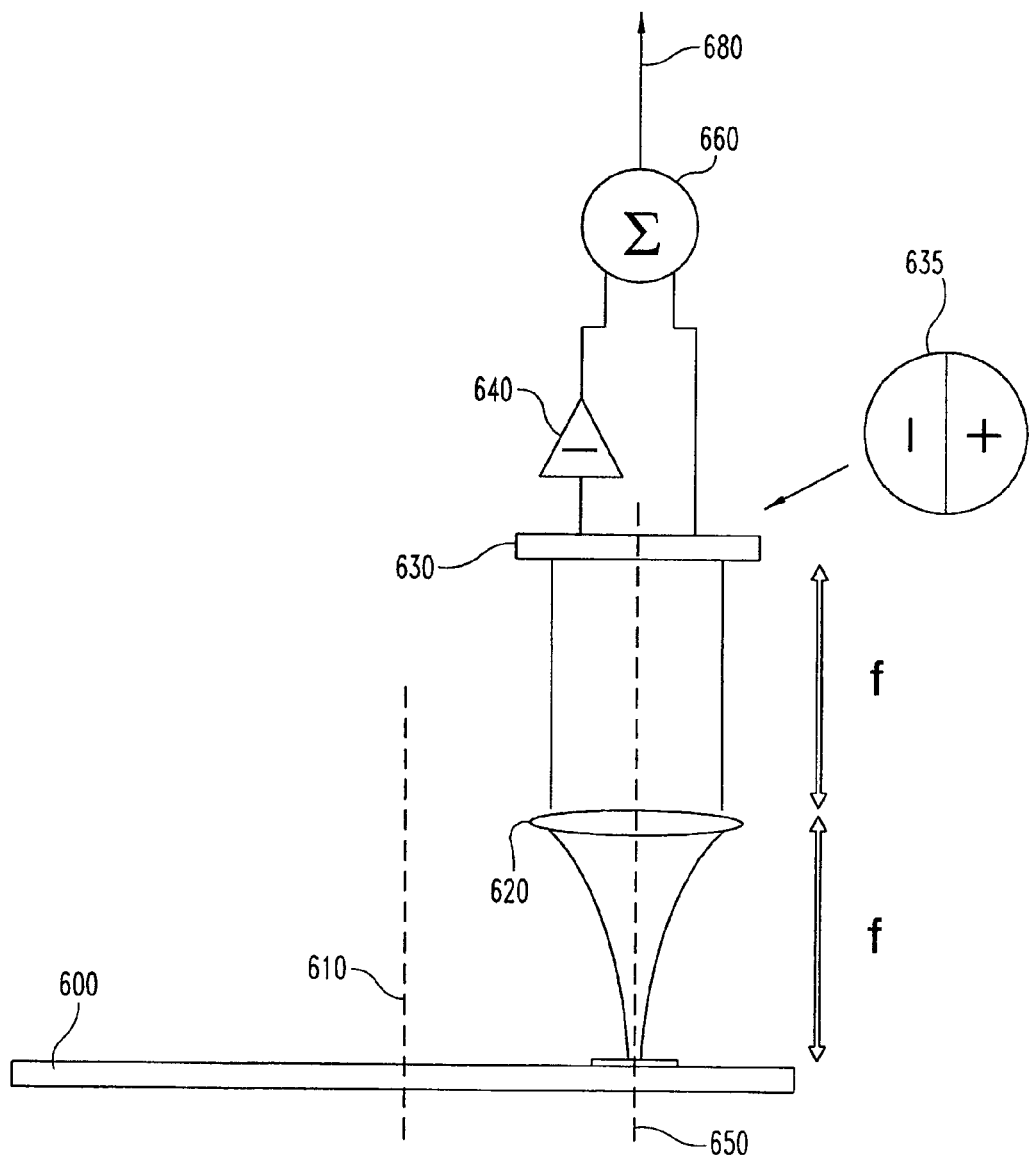
FIGS. 5A and 5B illustrate embodiments of the optical layout for step detection of a printed protein with slight variations in the split photodetector configuration.
Figure 5B:
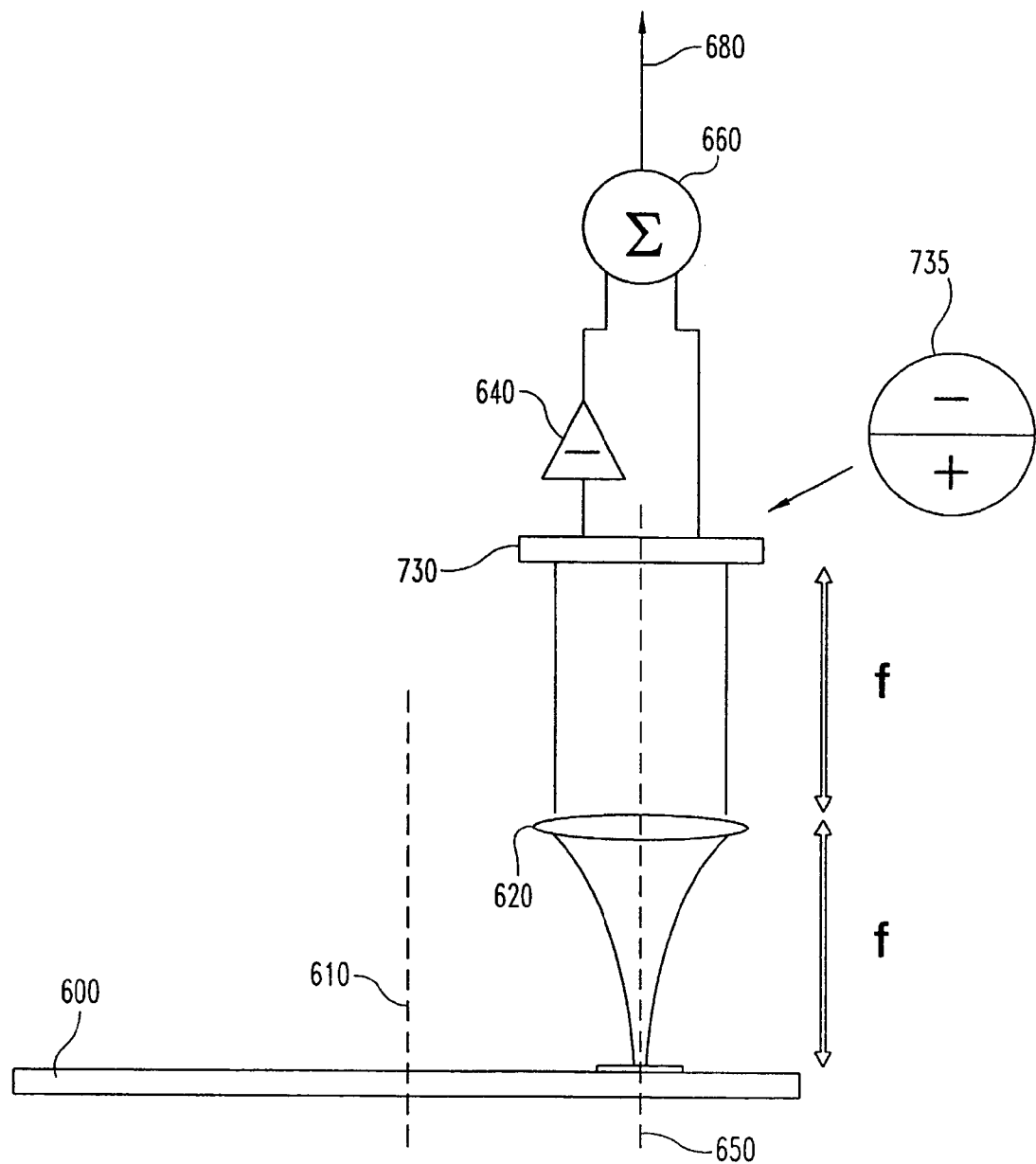

With reference to FIGS. 5A and 5B, there are illustrated two embodiments of an optical layout for step or slope detection of printed protein or other target molecules. It should be understood that like elements are labeled with the same reference numeral. Substrate 600 is preferably a spinning disk rotating about rotational axis 610. The optic axis 650 of the optical train may be moved radially inward or outward from the rotational axis 610 of substrate 600 to align it with, for example, some particular target region. An objective lens 620 having a focal length f is preferably utilized in the optical layout and is interposed between the substrate 600 and the photodetector 630 (FIG. 5A) or 730 (FIG. 5B). In the illustrated embodiments the objective lens 620 is spaced apart from the disk 600 by a distance f equal to the focal length of the lens and also spaced apart a distance f from the photodetector 630 (FIG. 5A) or 730 (FIG. 5B). In the embodiments of FIGS. 5A and 5B the photodetector 630, 730 is preferably a split photodetector that is split as indicated by 635, 735 respectively. It should be understood that various other embodiments of a split photodetector configuration are contemplated as within the scope of the invention. The photodetector may, for example, be a quadrant photodetector or a split-ring photodetector. Similarly, as previously discussed, in some embodiments of the present invention only half of the far field is collected with a knife-edge or other similar mechanism, and only half the possible signal is extracted (that half being substantially only one quadrature).

As illustrated in FIGS. 5A and 5B, the photodetector 630, 730 is positioned at the Fourier plane with the center line parallel to the long axis of the spoke to collect the differential signal between the two halves of the split photodetector. In the illustrated embodiments the signal from a portion of the split photodetector 630, 730 (corresponding to substantially one quadrature) is preferably sent through an inverter circuit 640 before being summed with the signal from another portion of the photodetector (corresponding to the other quadrature) via summing circuit 660 to produce output signal 680. Output signal 680 is a measure of the far-field intensity, and will vary as the probe laser beam scans across the substrate 600 (for example, as substrate 600 is rotated). Alternatively, as previously noted, only half the signal may be collected, preferably corresponding to substantially only one quadrature (though some relatively small amount of overlap of both quadratures might be tolerable without significant detrimental impact on signal-to-noise ratio).

Figure 6B:
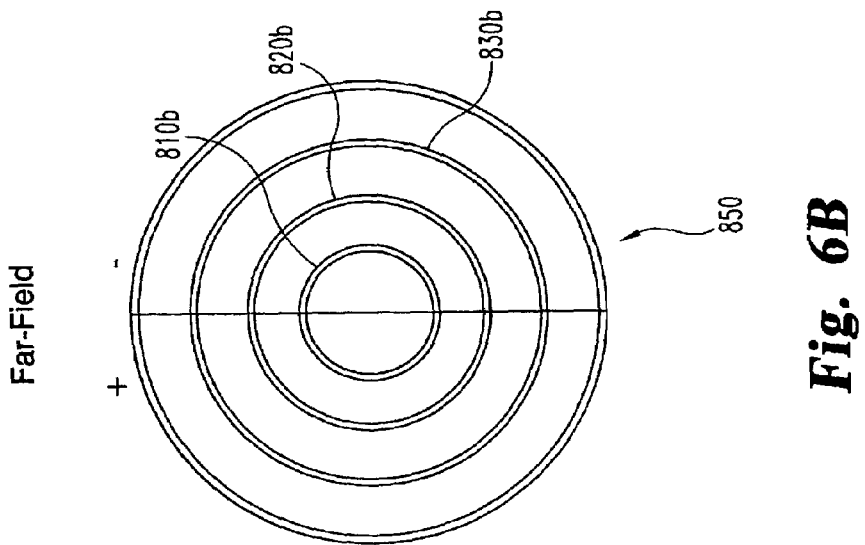
FIGS. 6A and 6B illustrate the scale-free nature of the step detection of one or more embodiments of the present invention.
Figure 6A:
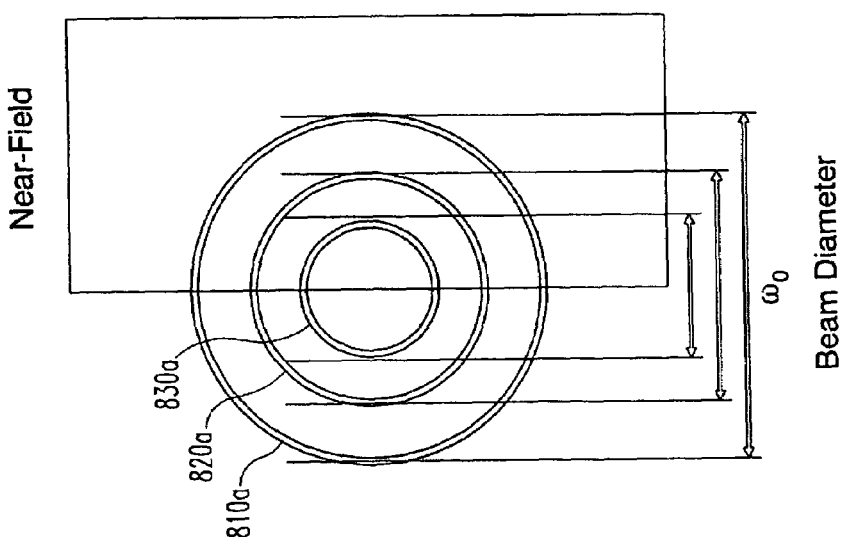

With reference to FIGS. 6A and 6B, there is illustrated the scale-free nature of the step or slope detection of at least some embodiments of the present invention. An edge has no intrinsic length scale. Therefore in the Fourier plane the edge aperture also has no length scale. This has the advantage that no matching of filter size with beam size (which may vary) is needed. As illustrated in FIGS. 6A and 6B, decreasing laser spot size (810a, 820a, 830a) simply leads to larger spot sizes (810b, 820b, 830b) on the split-photodetector configuration 850 that is preferably positioned at the Fourier plane. That is to say, changing the size of the laser spot size requires no change in the configuration of the split detector. Thus, the system is independent of the scale of the spot size or the spoke width, as long as the spoke width is larger than the beam diameter.

Figure 7B:
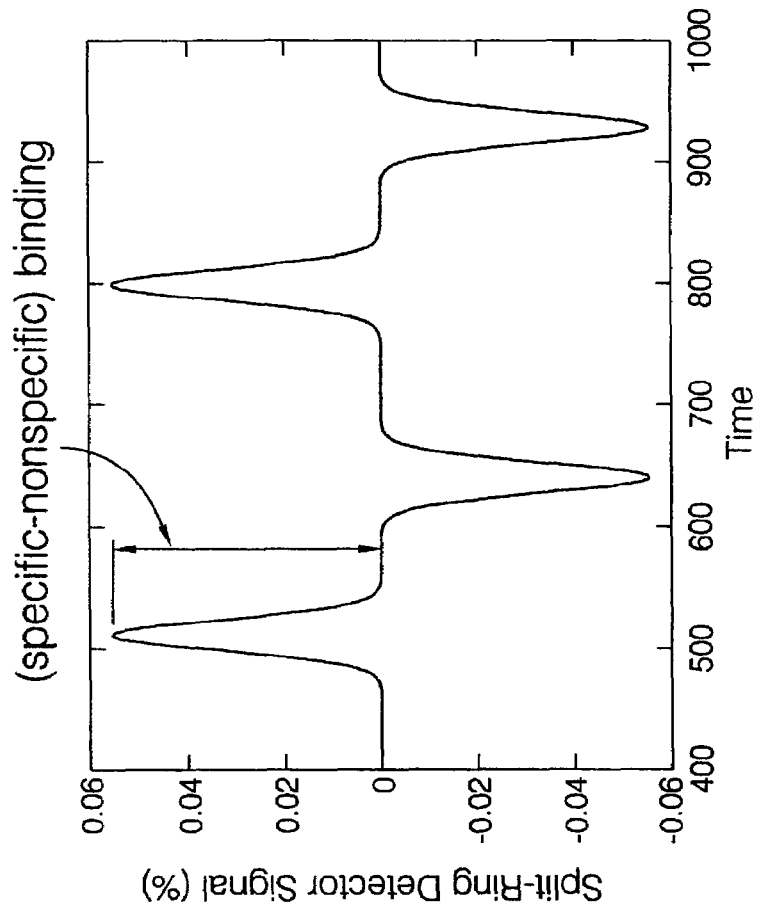
FIGS. 7A and 7B illustrate the direct subtraction of non-specific binding and the resulting time trace.
Figure 7A:
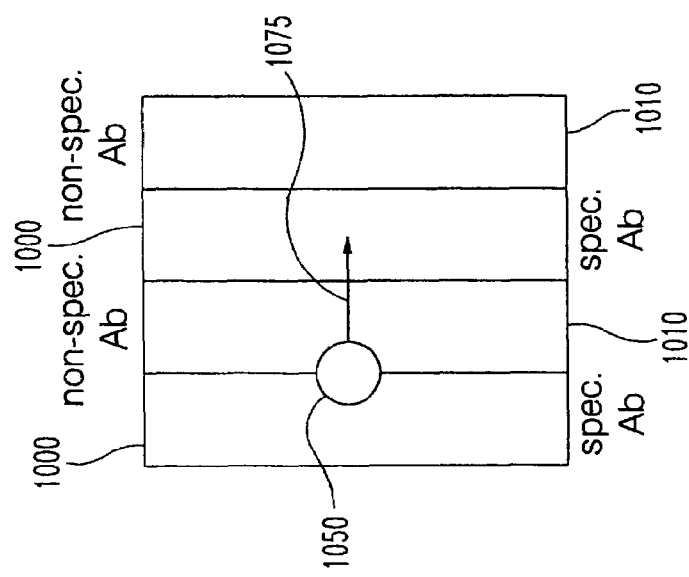

With reference to FIGS. 7A and 7B there are illustrated additional aspects potentially applicable to one or more embodiments of the present invention. Side-band detection without a carrier wave is preferably implemented simply as shown in FIG. 7A. Laser beam 1050 traces across alternating spokes of specific antibody 1000 and non-specific antibody 1010 along the direction indicated by the arrow 1075. The peak height at the edge of the spokes 1000, 1010 is simply related to the difference between specific and non-specific binding. Thus, there are no "separate" measurements of non-specific binding to subtract. With reference to FIG. 7B there is illustrated the direct subtraction of non-specific binding and the resulting time trace. The signal height depends only on the difference between specific and nonspecific binding. There is no carrier frequency, and all the detected intensity change is in the envelope. For further detail see U.S. Provisional Application No. 60/648,724, entitled "Method for Conducting Carrier-Wave Side-Band Optical Assays for Molecular Recognition" filed on Feb. 1, 2005, and also see U.S. application Ser. No. 11/345,566 being filed on the same day as the present application that claims priority to this provisional application and entitled "Differentially Encoded Biological Analyzer Planar Array Apparatus and Methods".

Figure 8:
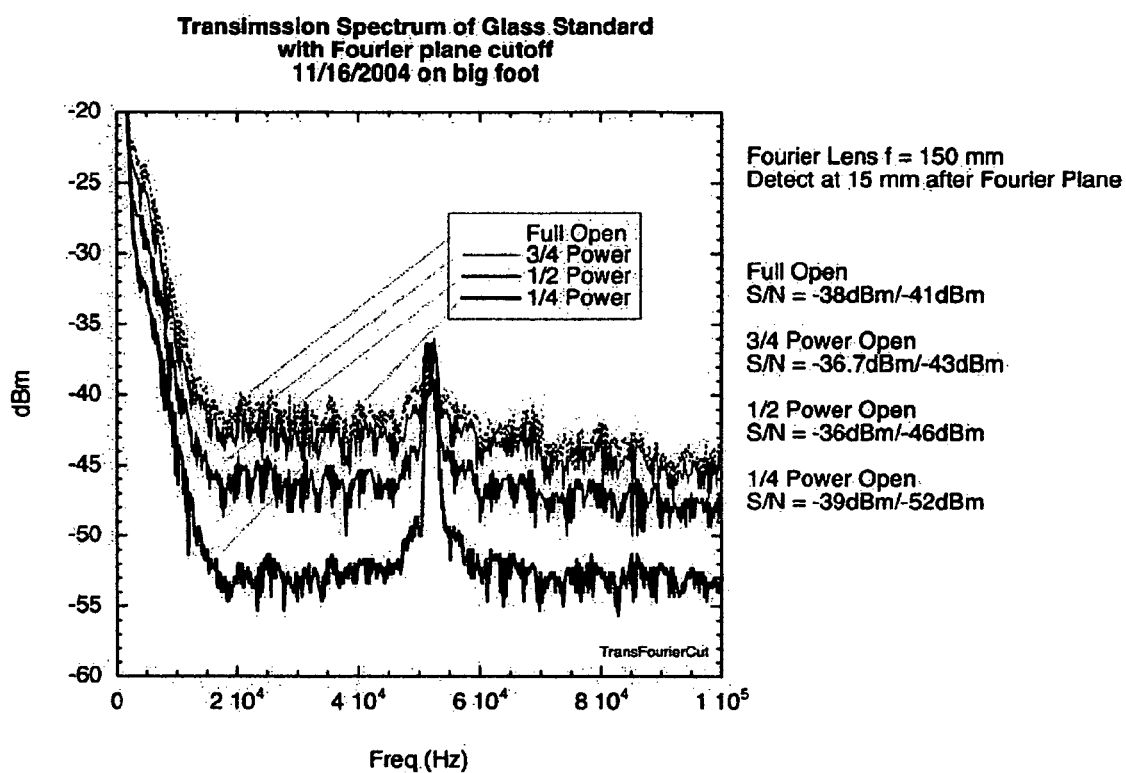
FIG. 8 illustrates the results of experimental demonstration of the knife-edge detection of spoke patterns on a calibration disk.

With reference to FIG. 8 there is illustrated data resulting from an experimental demonstration of the knife-edge detection of spoke patterns on a calibration disk. In one example according to the present invention, a calibration disk with 12 nm depth etched in a glass disk is utilized to demonstrate the experimental performance. The full field is detected in the top curve in FIG. 8, and the optimal signal condition is given at half-power for the second-from lowest curve. Suppressing the zero-order beam further lowers the noise floor for this transmission experiment in which the noise floor arises from heterodyning between the zero-order and light scattered from index variations in the glass.

Figure 9:
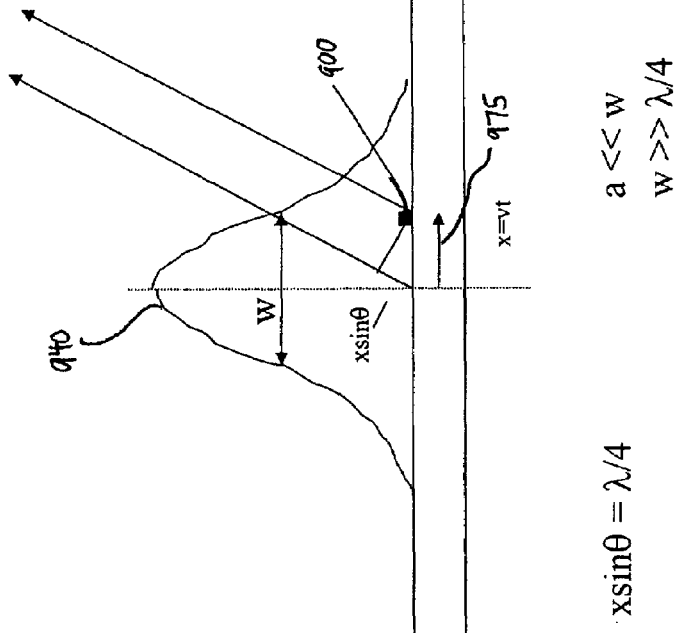
FIG. 9 illustrates single spoke detection.
Figure 10:
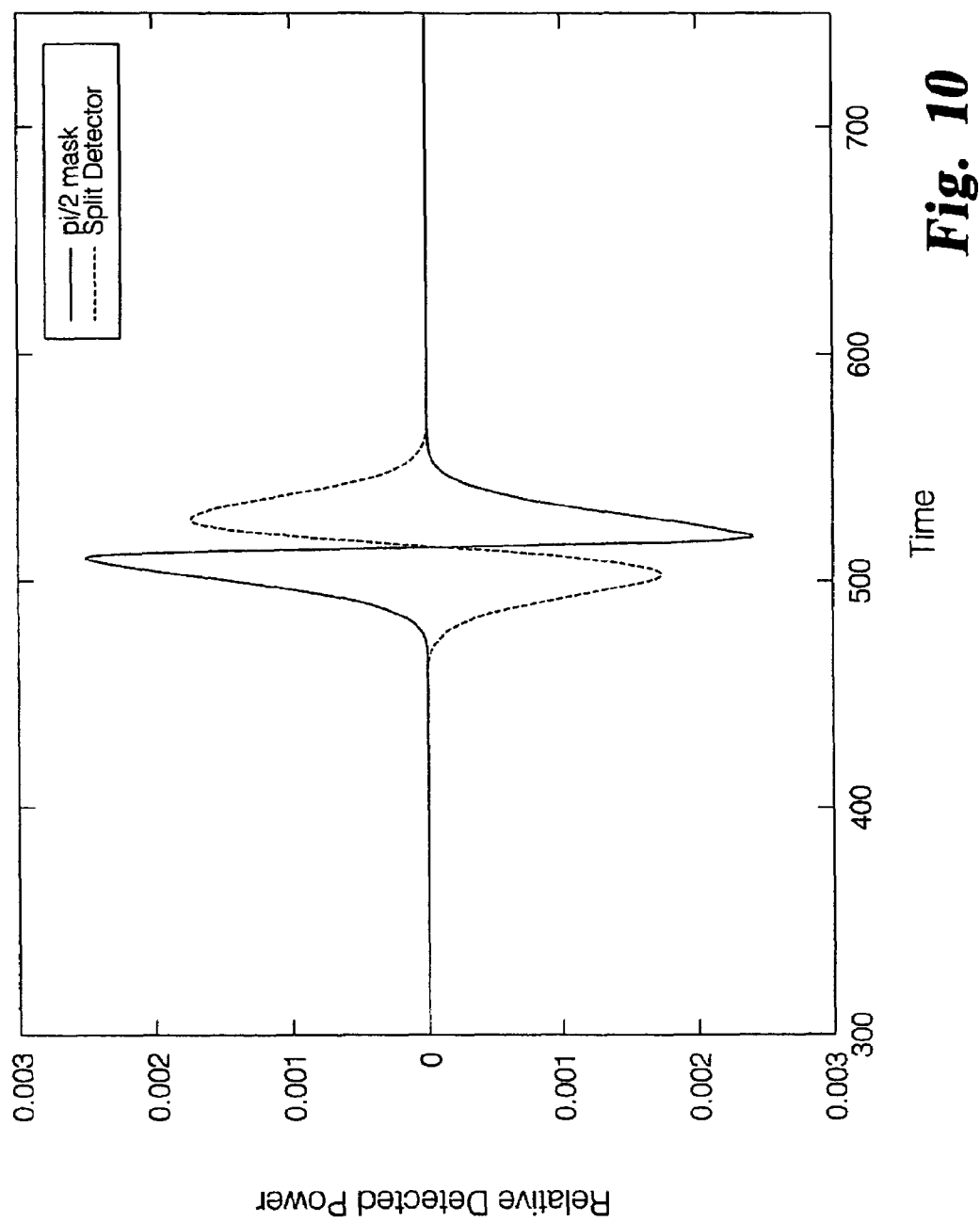
FIG. 10 illustrates detection of a very thin spoke or spot relative to the beam size for the case of the split detector (dashed curve) and a $\pi/2$ mask (solid curve).

With reference to FIG. 9 there is illustrated single spoke detection. In particular, there is illustrated detection of a very thin spoke or spot 900 relative to the beam 940. It should be understood that a spoke or spot with a size smaller than the beam width can still establish a condition of quadrature in the far field. In the embodiment illustrated in FIG. 9, a single small spoke or dot with a width a<<w, where w is the width of beam 940 (preferably a laser beam with a Graussian distribution as shown), can be detected. The small ridge can be detected using the same split-detector configuration as for wide spokes. But slightly higher performance is possible when a π/2 object mask is used in combination with an apertured detector, as shown in FIG. 10. As explained previously, the choice of masks at the different optical planes can maximize the constructive interference at the detector. The π/2 mask is especially useful in converting slopes and edges on the disk into intensity modulation at the detector. In special cases, the masks can remove the need for the split detector, allowing the full intensity to be detected in the far field. This approach simplifies the detector, but does require the addition of masks in the optical system.

The biological compact disk (BioCD) of and/or used with the present invention is a sensitive detection platform to, for example, detect patterned biomolecules immobilized on the surface of a spinning disk. Various embodiments of the present invention provide spinning-disk interferometry that allows high speed detection (10 microseconds per spot) of optical path length changes down to sub-nanometer scales with high repeatability. As previously mentioned, one important aspect in performing stable interferometry on a mechanically spinning disk is self-referencing: locking the phase of the signal and reference beams to quadrature (π/2 phase difference) independent of mechanical vibrations or relative motion.

It should be understood that the Phase-Contrast class (PC-class) of interferometric detection may be implemented in a wide variety of manners known to those of ordinary skill in the art. In one embodiment of the present invention, protein is immobilized using photolithography on a disk in a 1024 spoke pattern (it is contemplated as within the scope of the invention that the number of spokes may vary widely along with other design parameters). The step of the printed protein pattern diffracts a focused laser beam that is preferably detected in the Fourier plane with a split detector configuration including, but not limited to, split photodetectors, two separate photodetectors, a quadrant photodetector, and more generally a photodetector array. The signal from the split detector configuration might be differenced, which plays a role in the electronic domain similar to that of a phase plate in optical phase contrast imaging.

As will now be discussed further below, the potential of the PC-class in high speed label-free biosensing is demonstrated by a two-analyte immunoassay that shows good rejection of nonspecific binding and low antibody cross-reactivity. Immunoassays were performed against IgG immunoglobulins with detection of bound analyte below one picogram. To show the potential of scaling up to hundreds or thousands of analytes per disk, an experiment was also performed with small drops of protein solution.

A reflecting surface that supports a spatially-patterned biolayer diffracts a focused laser beam into an asymmetric far-field intensity pattern, as shown in FIG. 4. FIG. 4 illustrates a focused Gaussian beam 540 with waist $w_o$, incident on substrate 500. As previously derived above, a condition of quadrature exists between a ray passing through the biolayer 530 relative to a ray incident on the bare surface when observed at an angle given by $$\theta_Q = \sin^{-1}(\lambda/2w_o) \quad (1)$$

The largest change in intensity in the far-field diffraction pattern is caused by a sharp biolayer edge and is observed at this quadrature angle. There are two quadrature interference angles that have opposite signs at diffraction angles of opposite sign. When the total intensity is collected, the two signals cancel. To obtain the protein signal, a split detector with inversion and summation circuits is preferably used on the Fourier plane (examples of which are shown in FIGS. 5A and 5B, it being understood that other split detector configurations, such as a quadrant photodetector, are contemplated as within the scope of the invention). In the case of a sharp edge, the signal is linearly proportional to the phase shift caused by the protein layer, and therefore linear to the height of protein.

The change in the far-field caused by the patterned biolayer is given by $$\Delta E(\theta) = \int_{-\infty}^{\infty} K(\theta)(P(x,t)-1)E_{inc}(x)e^{ikx\sin\theta}dx \quad (2)$$

where $K(\theta)$ is the Fresnel factor, $\theta$ is the detection angle, $E_{inc}(x)$ is the field of the incident beam and $P(x,t)=e^{i\phi(x-vt)}$ is a phase function for the protein with a phase $$\phi(x,t) = \frac{4\pi}{\lambda}(n-1)h(x-vt)$$

for a biolayer with refractive index n and a varying protein height h(x) moving at velocity v. In our experiments, the function h(x) is approximately a square wave with a height of 8 nm and a refractive index of 1.33. The squared modulus of Eq. 2 gives the far-field intensity that is detected with a split photodetector with a difference channel. The resulting electronic protein signal is approximately proportional to the convolution of the beam profile with the first derivative of the protein height distribution dh(x)/dx. This technique is therefore a slope-detection technique. Sharper edges to the protein patterns produce stronger signals.

To better introduce the experimental discussion that follows the details of the apparatus and method used in obtaining the experimental data will now be discussed. It should be understood that these details are merely exemplary and a wide scope of variations of the same are contemplated as within the scope of the invention. The phase-contrast BioCDs are preferably fabricated from 100-mm diameter 1-mm thick borosilicate glass disks. The disks are preferably coated with a 10-layer dielectric stack of $Ti_2O_5/SiO_2$ that serves as a laser mirror with a center wavelength at 633 nm. There are several different ways of immobilizing protein onto the disk surface. Protein can be immobilized onto the surface using physical adsorption through 1) silanization of the silica surface, 2) covalent binding of biotin-avidin for high-affinity immobilization, or 3) covalent binding to ATPES Epoxide surface coating.

The reflecting surface of the BioCD disk is preferably a dielectric medium that may have multiple layers to enhance the reflection of light and to maximize the magnitude of the electric field at the surface. A quarter-wave stack is one of the most common dielectric structures used to achieve these conditions, but oxide layers, for instance on silicon, can also be used.

Silanization follows a standard protocol using chlorooctadecylsilane treatment of the silica surface. Proteins bind through hydrophobic interaction with the organic end groups. Patterning of the protein is preferably accomplished by a gel stamp method.

In the high-affinity biotin-avidin process the surface is covered with a poly-succinimide polymer that is conjugated with biotin. Photolithography is then applied in which photoresist is spun on top of the poly succinimide polymer coating and exposed through, for example, a 1024-spoke photomask and developed. The disk surface is then exposed to avidin which attach to the biotin in the exposed regions. Biotinylated antibodies are then added and attach to the avidin that binds in the exposed regions.

The APTES Epoxide coating follows a standard protocol. Photolithography is applied and the disk is treated with a 1% Sodium Borohydride solution that etches the exposed disk surface. After the photoresist is removed, the disk has a patterned surface that covalently binds proteins. Both physical adsorption and covalent binding to the surface produce protein patterns with sharply defined edges in a spoke pattern that sweeps through the probe laser spot when the disk spins.

In one embodiment, the optical detection system preferably uses a 5 cm focal-length objective lens to focus a 635 nm wavelength diode laser beam on the disk to a diameter of approximately 20 microns. The reflected and scattered light is split by a beam splitter and directed to a quadrant photodetector placed at the Fourier plane of the objective lens. The quadrant detector preferably has three output channels: the total intensity, the difference between the upper and lower halves, and the difference between left and right. Depending on the orientation of the protein spokes, one of the difference channels gives the desired phase signal. The other difference channel provides a diagnostic for alignment and disk wobble, while the summed channel provides amplitude information related to Rayleigh and other scattering losses from the disk that are small or negligible for uniform protein printing.

Figure 11:
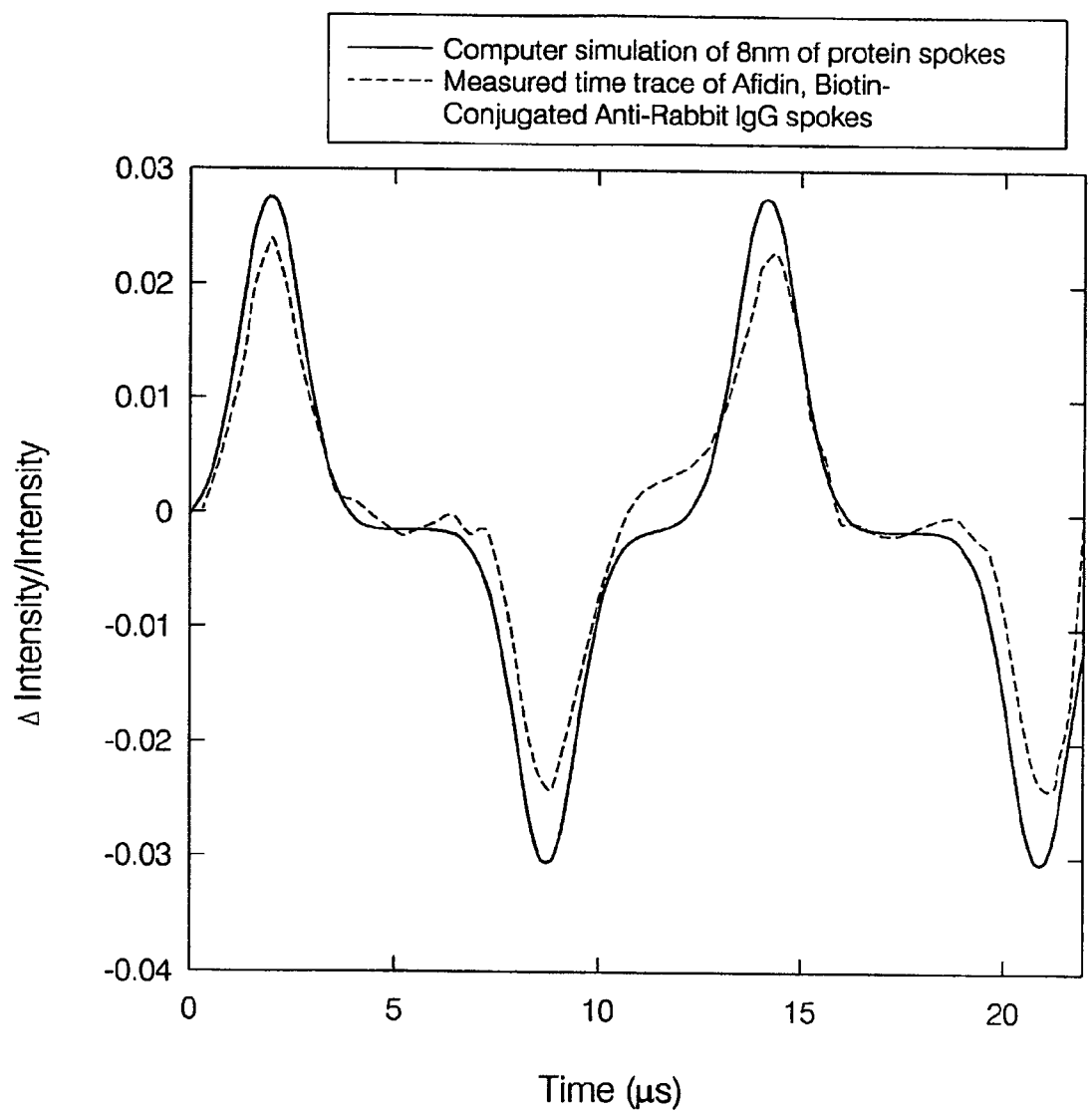
FIG. 11 illustrates the measured time trace of protein spokes compared to computer simulation of 8 nm protein spokes.
Figure 12:
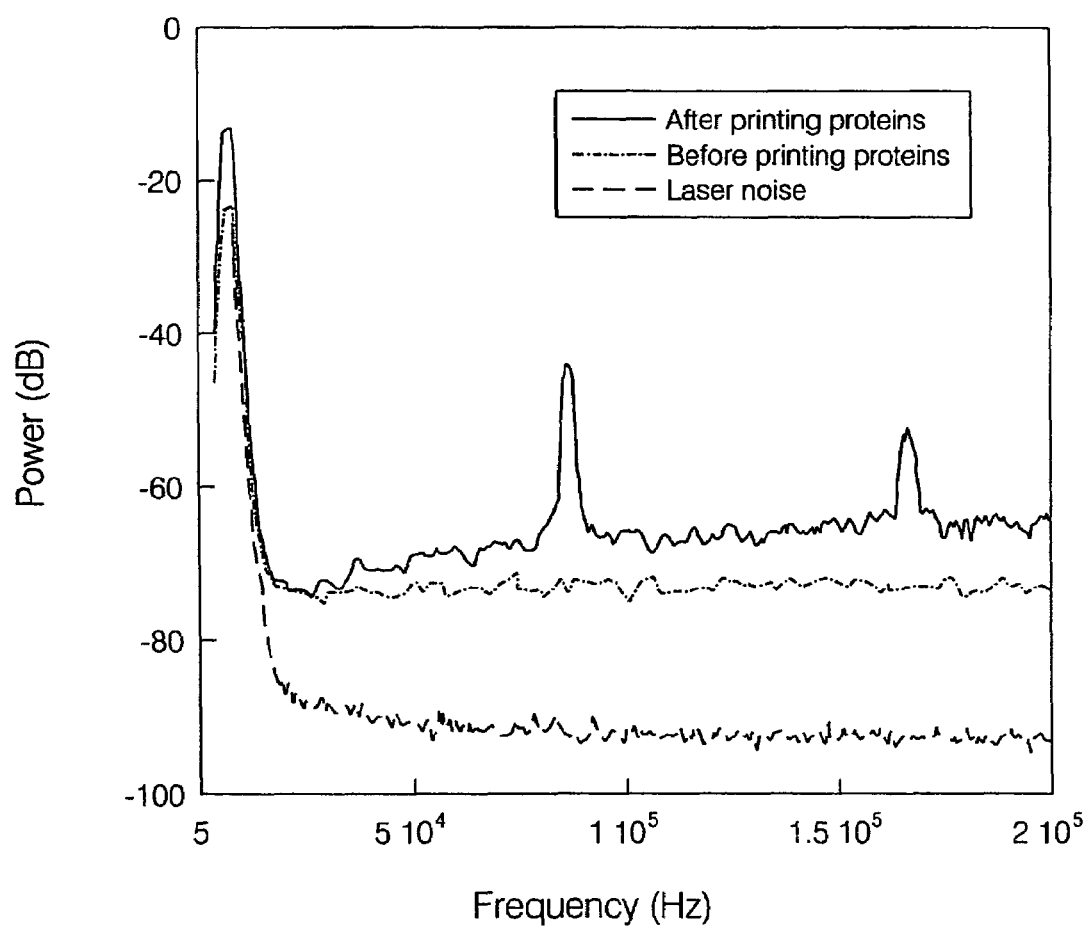
FIG. 12 illustrates the measured power spectrum of protein signal.

The disk is preferably rotated at a constant frequency of 80 Hz on a stable spinner (Lincoln Laser, Inc.) producing a time-dependent phase and amplitude signal as the protein spokes pass through the focused laser spot. FIG. 11 shows the measured time trace of photolithography printed FITC-conjugate Avidin (Sigma) and Biotin-conjugated Anti-Rabbit IgG (Sigma) double protein layer, compared with a computer simulation assuming 8 nm in height and 100 micron wide protein spokes. FIG. 12 shows the electrical power spectrum of the signal detected with a 3-kHz-bandwidth. The noise from surface roughness, which is distributed across the multiple interfaces of the dielectric stack, is 15 dB higher than the noise floor of the detector and laser system. The protein signal from the protein spokes has a 25 dB signal-to-noise ratio.

To demonstrate the potential of implementing the PC-class Bio-CD as an immunoassay, we performed specific antigen-antibody binding in a binary assay. Fluorescene-conjugated bovine serum albumin (FBSA) was printed using a patterned poly-acrylamide gel permeated with FBSA brought into direct contact with the dielectric coated glass disk. For this experiment the surface was activated with chlorodimethyloctadecylsilane. At the regions of contact between the poly-acrylamide gel and the surface, proteins diffuse out of the gel and are immobilized by physical adsorption. The quality of the printing technique was tested with fluorescence imaging and atomic force microscopy. The BSA is relatively inert, and produces a universal carrier template on the disk surface that can then be backfilled (in the spoke regions between the BSA) with active or inert proteins or other control molecules.

The disk is then backfilled with specific antigen molecules. The BSA-printed disk was partitioned into four 90-degree quadrants. The unprinted land in each of the four quadrants was backfilled with four different chemistries: 1) phosphate buffer, 2) rabbit IgG, 3) FBSA and 4) horse IgG, respectively. The concentration of all backfilling protein solutions were 20 μg/ml. The prepared disk was then incubated in bands against specific recognition molecules. Three annular bands, when crossed with the four quadrants, created a total of 12 virtual "wells" to serve as specific assays with numerous control assays. The inner band was incubated with anti-horse IgG, and the outer band was incubated with anti-rabbit IgG, both with concentrations of 20 μg/ml. The middle band was not incubated against a target sample, but experienced the same wash steps as all bands, and hence gave a measure of the stability of the assay and served as a negative control. Of the 12 wells, 4 were control wells to measure wash-off systematics, 4 were control wells to measure non-specific binding of antibodies to BSA, 2 tested for antibody-antigen cross-reactivity, and 2 tested specific antibody-antigen binding.

Figure 13:
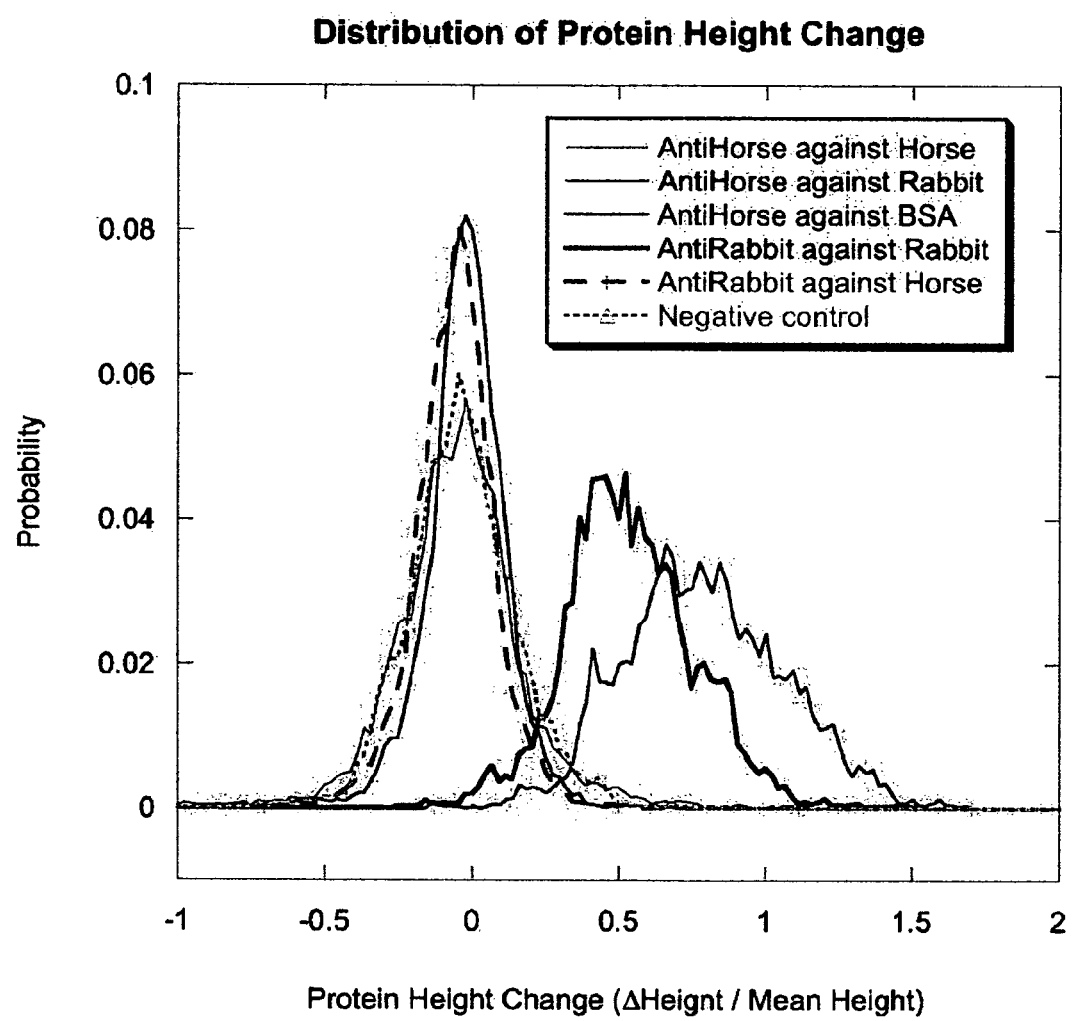
FIG. 13 illustrates the distribution of the changes of protein height in different segments of the disk after incubation.
Figure 14:
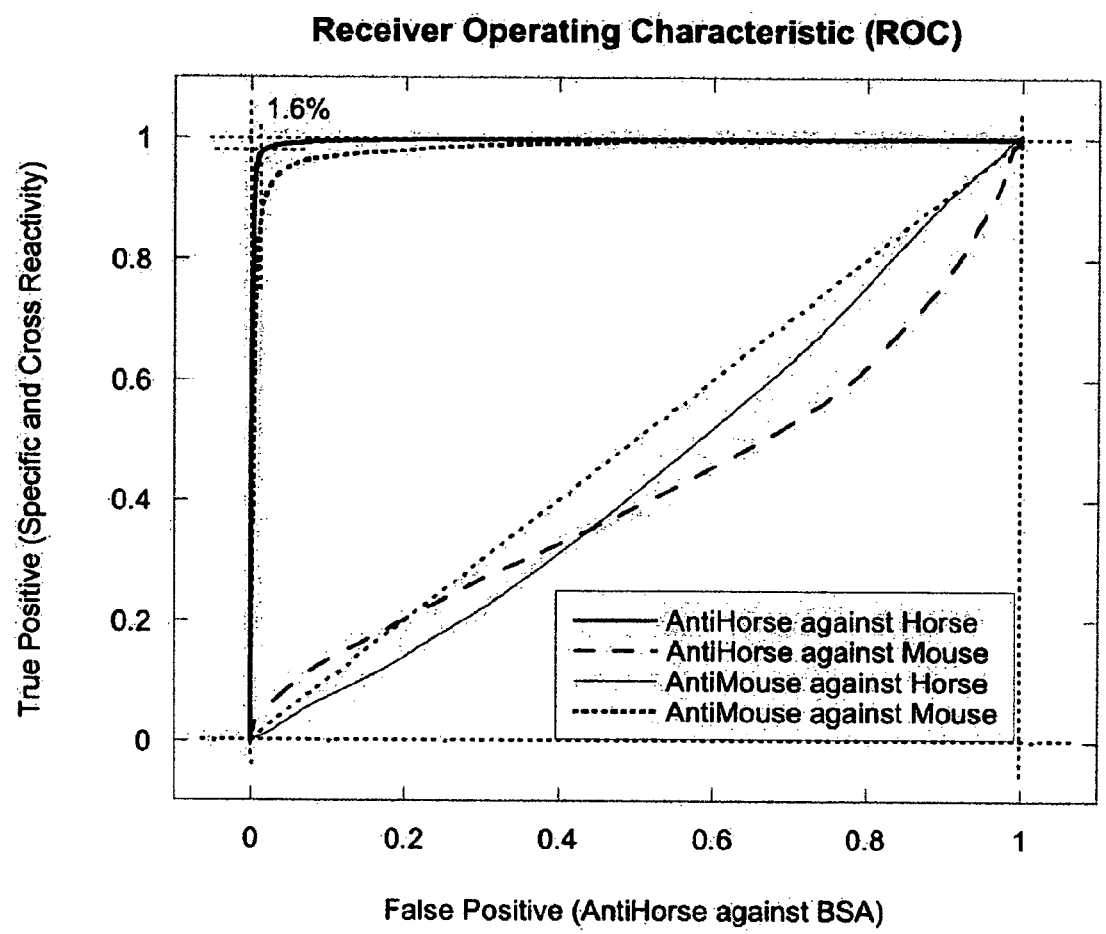
FIG. 14 illustrates the Receiver Operating Characteristics of the binary assay.
Figure 15:
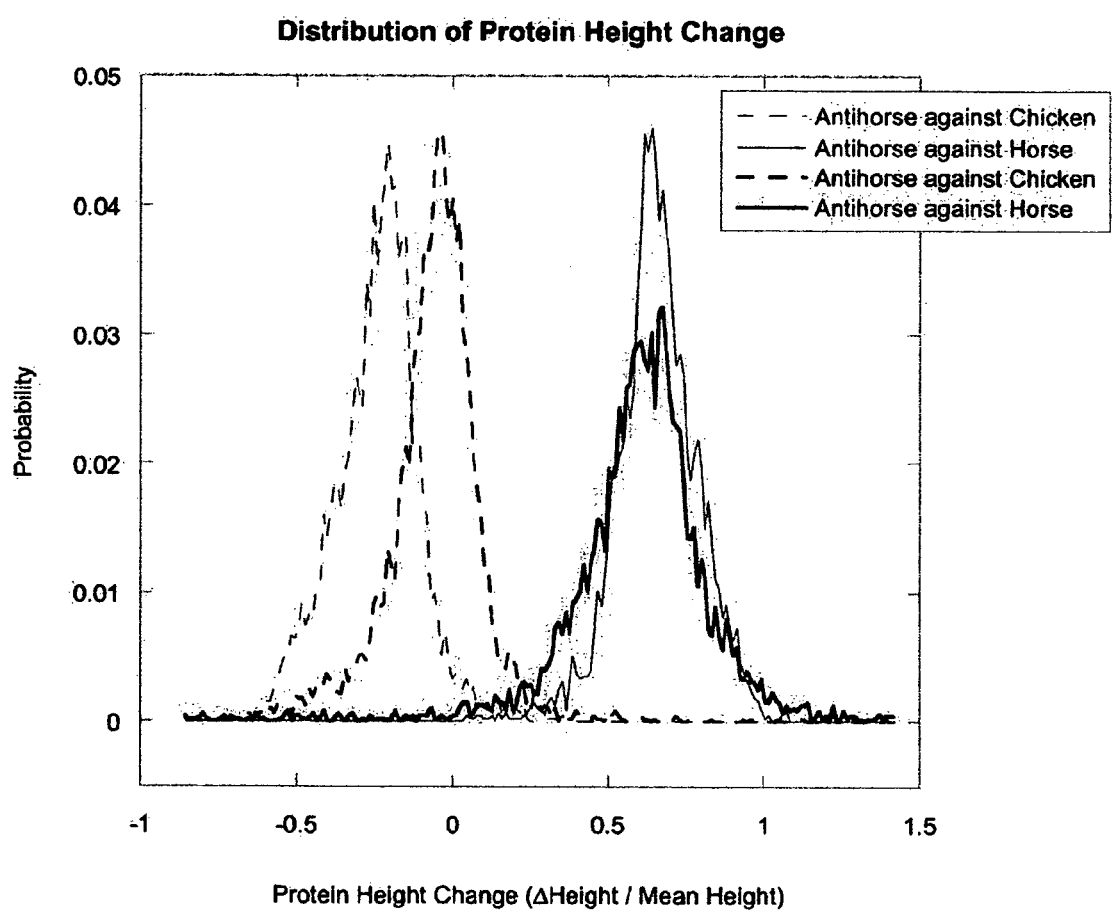
FIG. 15 illustrates the distribution of the changes of protein height in different protein drops after incubation.

The results of the assay are shown in FIGS. 13 and 14. Distribution of height change in different segments after exposure to antibodies are shown in FIG. 13. The two specific assays behave significantly different than the others, and there is not much difference between negative controls, non-specific binding of antibody to FBSA and cross reactivity (CR) where anti-horse was applied against rabbit, and anti-rabbit was applied against horse. This shows that there was no significant cross-reactivity or non-specific binding in the experiment. The two specific binary assays (anti-rabbit binding to rabbit and anti-horse binding to horse) had responses of 60% and 80%. The standard deviations were 20% and 30%, respectively. FIG. 14 shows the Receiver Operating Characteristic (ROC) curves of this experiment. The non-specific binding segments are used as false positive. The curves show distinct differences between specific and non-specific binding, and there is little difference between cross reactivity and non-specific binding. The p-value is calculated to be less than 0.01 from the distributions.

To test the variability of the optical detection process, prior to this experiment, a disk printed with FBSA by gel-stamp printing on a physical adsorption surface was dismounted, remounted with an overall rotation of 90 degrees and scanned again four times, and all values repeated to within a standard error of 5%. If the disk is remounted without rotation, the standard error falls to less than 2%. Therefore, the optical detection is stable and repeatable with sufficiently small standard error for future tests of dose response, preferably after the immobilization and incubation chemistries are made more uniform.

To demonstrate the possibility to scale up to hundreds or even thousands of assays per disk, an experiment with spotted protein solution was performed on an APTES Epoxide surface coating. After photolithograqphy, the disk was soaked in 1% Sodium Borohydride in deionized water solution for twelve hours. The exposed surface was etched by the solution and became extremely hydrophilic so that it did not tend to attract proteins. After removing the photoresist, the covered part of the disk still had an APTES coating that strongly binds proteins. Regions of horse IgG and chicken IgG were spotted onto the disk. The size of the regions was about 10 mm. Then the regions of proteins were incubated with spots of anti-horse IgG of the same size. The distributions of protein height change in different drops are shown in FIG. 13. The distinction between specific and non-specific binding can be clearly seen here, with a p-value calculated to be less than 0.01. Although the size of the drops in this experiment was 10 mm, it can be easily reduced to 1 mm or even less by an ink-jet printer, therefore making it possible to perform thousands or even more assays per disk.

Having now described the results of some experimental data, additional features and potential advantages of select embodiments that may or may not include such features of the present invention will be described. It will be understood that the present invention relates generally to a self-referencing interferometric optical biosensor that measures phase modulation from proteins on spinning disks. The optical detection of the patterns at high speed yields low noise floors far from 1/f noise. Periodic protein patterns on the disk provide a spatial carrier frequency that is preferably demodulated to yield a slowly-varying protein envelope that can be differenced with high accuracy.

In one embodiment of the present invention, two consecutive differential scans of a disk are differenced without any disk dismount, yielding an rms surface height measurement error of only 20 pm corresponding to 5 femtograms of protein within a focal spot diameter of 20 microns. Simple area scaling relations are discussed below that predict the performance of immunoassays as a function of well size. Also discussed below is a demonstration of a surface mass sensitivity for a differential phase contrast BioCD down to 0.2 pg/mm. This BioCD sensitivity is comparable to the sensitivity of surface plasmon resonance sensors, but is preferably achieved without resonant structures and hence is relatively easy to fabricate and operate.

With the above two paragraphs as introduction, further details will now be discussed in the use of differential phase contrast detection in conjunction with spatially patterned protein that provides a spatial carrier frequency that is frequency-demodulated to yield the slowly-varying protein envelope. The optical detection of the patterns at high speed yields low noise floors far from 1/f noise. Two consecutive differential scans of a disk are differenced, yielding an rms surface height measurement error of only 20 pm corresponding to 5 femtograms of protein within a focal spot diameter of 20 microns. With the appropriate scaling with size, a surface sensitivity of 0.2 pg/mm is preferably obtained.

With respect to the same, the optical scanning system is preferably a differential phase contrast system as previously discussed herein. Such a system preferably comprises a stable motor (Lincoln Laser), a 635 nm laser light source (Coherent) and a split quadrant detector with an output signal that is differenced between the channels perpendicular to the motion of the disk surface. The net signal is thus proportional to the first spatial derivative of the disk surface height, or in the case of a disk carrying patterned protein, the derivative of the protein surface mass density where we assume that the phase modulation is proportional to the surface density.

In one embodiment of the present invention, the BioCD disk is a multilayer dielectric mirror with a center wavelength at 635 nm. The top $SiO_2$ surface of the disk was patterned with avidin on a biotinylated poly-succinimide polymer coating attached through silanes to the silica surface. The avidin pattern comprises a series of ridges with a spatial periodicity that varies linearly as a function of disk radius. A typical period is about 150 microns. The disk is spun at 5000 rpm and the laser is focused to a spot diameter of 20 microns. The detection frequency is typically 50 kHz, which is far from the 1/f noise of the laser and electronic amplifiers. The optical performance is within one and a half orders of magnitude of the shot-noise limit. It should be understood that a wide variety of operating parameters are contemplated as within the scope of the invention. The above referred to spatial period, disk rotational speed, focused laser spot diameter and detection frequency are merely exemplary.

Figure 16:
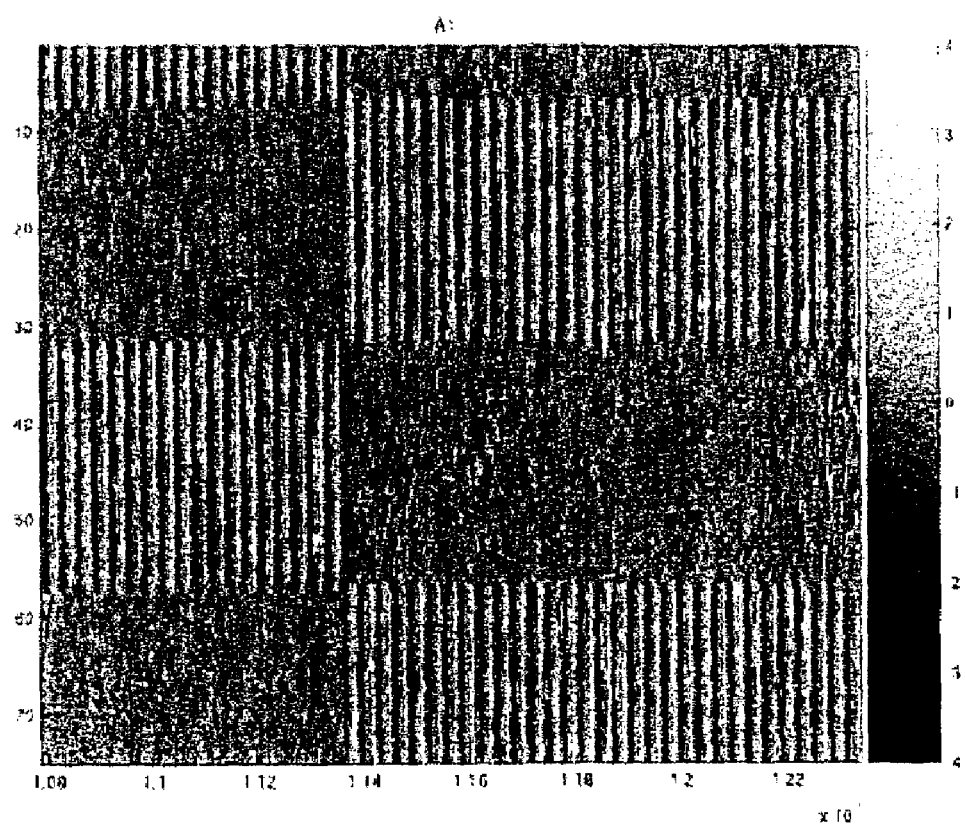
FIG. 16 illustrates the spatial topology of printed avidin ridges on a BioCD.
Figure 17:
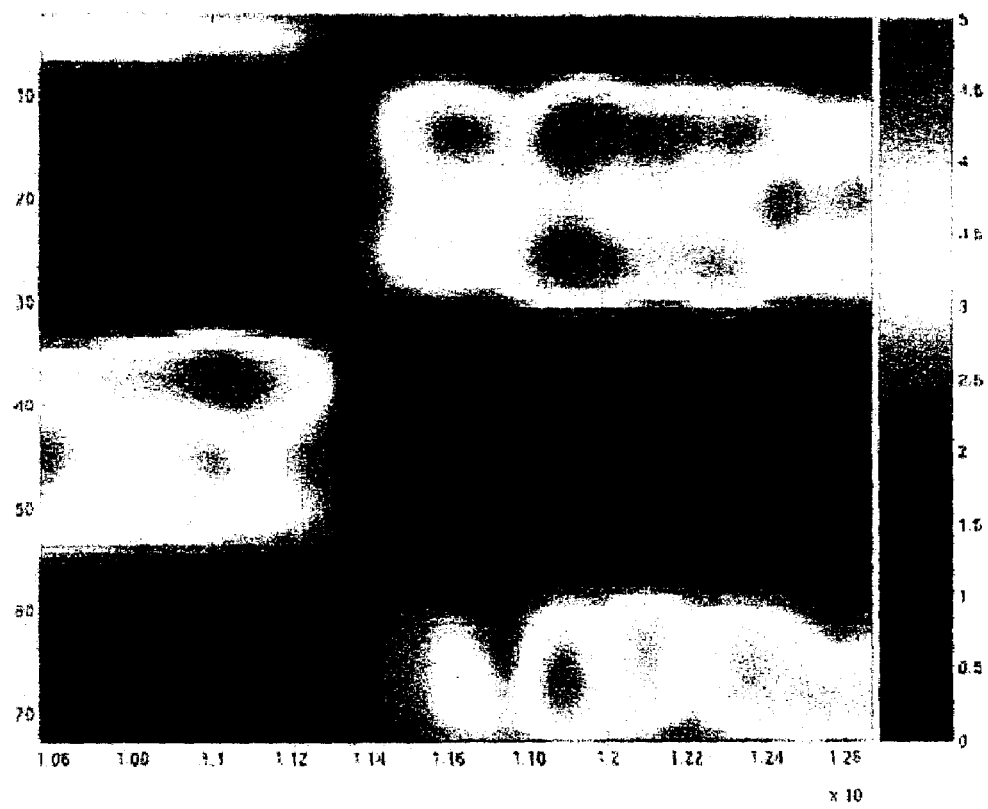
FIG. 17 illustrates the spatial frequency demodulated image of the disk of FIG. 16.

With reference to FIG. 16, there is shown the surface topology of the protein spokes for a selected portion of the disk. The differential signal appears to the eye as a 3D topology with shadows. The bright signal is from a leading protein step, while the dark negative signal is from the corresponding trailing step. The spatial carrier frequency is demodulated to obtain the envelope function of the protein, shown in FIG. 17. The envelope is slowly varying on the scale of the laser probe beam. As previously mentioned, in various embodiments of the present invention the difference between two consecutive scans is preferably determined.

Figure 18:
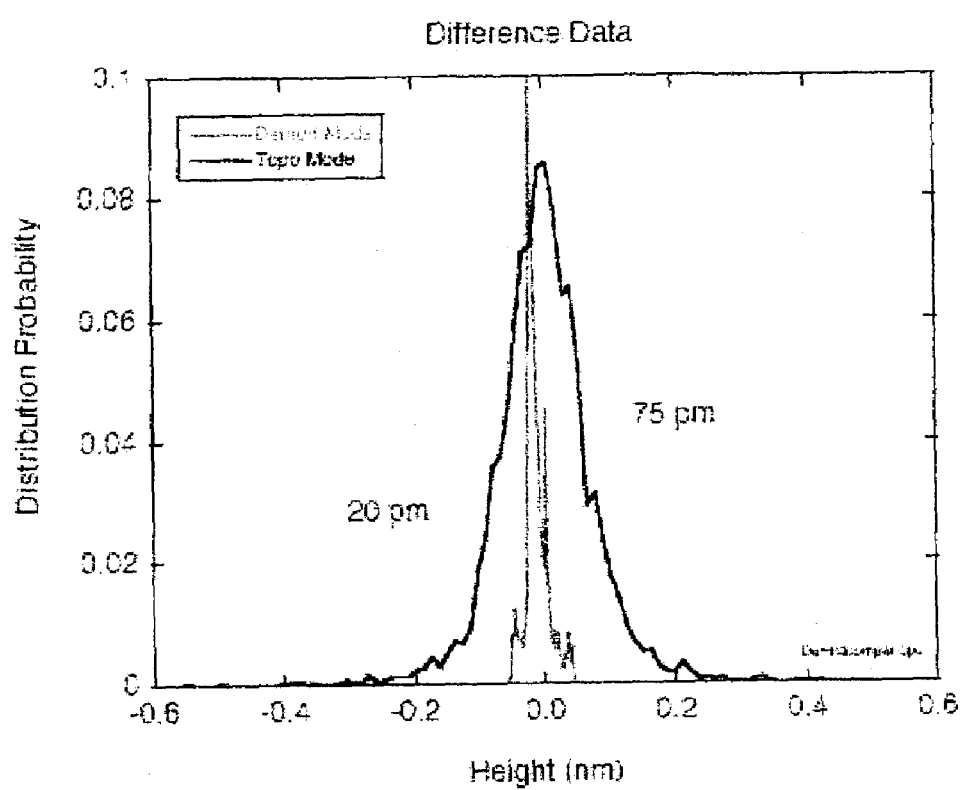
FIG. 18 illustrates a histogram of avidin differential height on the BioCD obtained without dismounting the disk.

Histograms of the differenced data between two consecutive scans are shown in FIG. 18. Without demodulation, the width of the distribution of heights is 75 pm. After demodulation the distribution is only 20 pm. This is the average height measurement error per focal spot area. It is dominated by the mechanical performance of the system (repositioning error between scans) and is not limited by the laser stability nor is it a fundamental limit. This surface height uncertainty can be translated into the surface mass sensitivity for the differential phase contrast BioCD.

The fundamental scaling assumption made in the derivation below is the assumption of an uncorrelated random distribution of measurement errors on two successive scans of a BioCD surface height distribution. Departure from these conditions will be discussed briefly, but these assumptions are relevant for usual conditions encountered with the BioCD. Deviation from the assumption of an uncorrelated random surface roughness would lead to different scaling and hence different values of mass per area. For instance, if the errors in the differenced surface measurements are spatially correlated, then $S_{mm}$ would increase compared to the value derived below (with a limiting value of about 10 pg/mm$^2$ in the current system, although with system stability improvements this number would be smaller).

From FIG. 18 the uncertainty in the surface height between two repeated disk scans was determined to be 20 pm per focal spot, corresponding to 5 femtograms of protein per focal spot with a diameter of 20 microns. The surface mass sensitivity associated with this measurement is 0.004 pg/(0.02 mm)$^2$=10 pg/mm$^2$. But to compare with other surface mass detection techniques, such as surface plasmon resonance, this number needs to be scaled correctly to the corresponding size of 1 mm under the conditions of uncorrelated random surface roughness that reduces the standard error of a measurement by the square root of the sensor area. The equivalent scaled surface height sensitivity at the scale of 1 mm is given by $$\Delta h_{mm} = \Delta h_{meas} \sqrt{\frac{w_{meas}^2}{1 \text{ mm}^2}} \quad (3)$$

where $w_{meas}$ was the spot diameter associated with the measured height difference $\Delta h_{meas}$. For $\Delta h_{meas}$=20 pm and $w_o$=20 microns this gives $\Delta h_{mm}$=0.4 pm. It is interesting to note that this average surface height sensitivity is less than the radius of a proton. The mass associated with this protein height is $$\Delta m_{mm} = \Delta h_{mm} \rho_m 1 \text{ mm}^2 \quad (4)$$

which, for $\Delta h_{mm}$=0.4 pm gives $\Delta m_{mm}$=0.2 pg.

To obtain the general scaling for surface mass sensitivity, equations (3) and (4) are combined to give $$\Delta m_A = \Delta h_{meas} \sqrt{\frac{w_{meas}^2}{A}} \rho_m A \quad (5)$$

from which the sensitivity is determined as $$S = \frac{\Delta m_A}{\sqrt{A}} \qquad (6)$$
$$= \rho_m \Delta h_{meas} w_{meas}$$
$$= 0.2 \text{ pg/mm}$$

which has the units of mass per length.

For a single assay that distributes sensors over an area A, the minimum captured mass that can be detected from that assay is given by $$\Delta m_A = S\sqrt{A} \qquad (7)$$

As an example, if the assay area is 1 mm², then the detected mass is 0.2 pg.

From this, we conclude that the correctly scaled surface mass sensitivity at a square millimeter is $$S_{mm} = \frac{S}{\sqrt{1 \text{ mm}}} = 0.2 \text{ pg/mm}^2 \qquad (8)$$

This area-dependent sensitivity is comparable to the best values determined by SPR. This sensitivity is gained without the need for resonance and hence is much more robust and easy to manufacture than other interferometric approaches or resonance approaches that rely on resonance to provide high sensitivity.

The square-root scaling of equation (7) is the consequence of signal averaging over larger areas. This provides measurements on the BioCD with a strong advantage. The sensitivity per focal spot attained through the sensitivity of interferometry is increased by the signal averaging over areas that are many times the area of a single focal spot. For instance, a 20 micron diameter spot goes into an area of 1 mm² a factor of 50 times. The square root of this is an improvement by a factor of 7, or nearly an order of magnitude.

The performance of the PC-class BioCD falls between the previously discussed performance of the MD-class and the AO-class by presenting useful trade-offs. The phase contrast signal is significantly stronger than for the MD-class and the immobilization is more uniform on the silica surface. On the other hand, the PC-class detects the derivative h'(x) of the protein pattern on the disk, while the AO-class responds directly to the protein profile h(x). The AO-class approach was also more stable because of its active adaptability, but is more difficult to implement. As an example, with respect to the AO-class related disclosure found in U.S. Published Application No. 2004/0166593A1 there are illustrated photodetectors 444A and 444B. In the AO-class, however, the two beams are distinct and separate, arising from distinct spatial modes. The two beams also carry very different information, with the "direct" beam carrying mostly amplitude information and the "diffracted" beam carrying phase information. Thus, the photodetectors 444A and 444B A of FIG. 21 of U.S. Published Application No. 2004/0166593A1 combine phase and amplitude rather than separating them out. However, in the PC class, there is preferably only a single generating spatial mode that is scattered antisymmetrically. When this scattered light is detected and differenced in the split-photodetector configurations of the present invention, only the phase information is retrieved. The amplitude information is obtained by simply detecting all the light.

Collectively, the advantages of the PC-class with the easy disk fabrication and simple detection give this new BioCD quadrature class good prospects to pursue high-multiplicity multi-analyte assays. The PC-class is a class of surface-normal self referencing interferometers on the free surface of spinning disks preferably without resonant structures. The interferometric elements preferably have surface areas as small as the focal spot of a laser, with interaction lengths that are only as long as the thickness of the biolayer and without any reliance on optical resonance that can make structures difficult to manufacture.

The above described detection systems are described and illustrated with a Bio-CD configured to utilize a reflected signal beam such that the detection system(s). It should be understood that it is contemplated as within the scope of the invention that the present invention also encompasses detection systems configured for use with a Bio-CD configured to produce a transmitted signal beam.

It should be understood that although the Bio-CD and associated detection systems have been described for use in detecting the presence of blood proteins in a biological sample, the Bio-CD and associated detection systems may be utilized for additional applications such as the analysis of environmental samples including water or other fluidic samples.

While the present system is susceptible to various modifications and alternative forms, exemplary embodiments thereof have been shown by way of example in the drawings and will herein be described in detail. It should be understood, however, that there is no intent to limit the system to the particular forms disclosed, but on the contrary, the intention is to address all modifications, equivalents, and alternatives falling within the spirit and scope of the system as defined by the appended claims.

What is claimed is:

1. A label-free phase-contrast quadrature interferometric method of detecting the presence or absence of a target analyte in a biological sample, comprising:
exposing a reflecting surface of a substrate to the biological sample, the reflecting surface having a spatial pattern of coatings of receptor molecules, each coating specific to a particular target analyte; and
using a split-photodetector to measure intensity in a far-field diffraction pattern of a reflected signal resulting from a focused probe laser beam having a wavelength λ that is incident with waist $w_0$ on the spatial pattern of coatings of receptor molecules while scanning at least a portion of the substrate;
wherein intensity is measured of a portion of the reflected signal in a substantially quadrature condition by measuring intensity with the split-photodetector of at least one of two observation angles substantially equal to a pair of quadrature angles, the quadrature angles $\Theta_q$ being defined from a ray normal to the substrate by a formula:

$$\Theta_q = \sin^{-1}(\lambda/2w_0).$$

2. The method of claim 1, further comprising inverting an output of the split-photodetector at one of the pair of quadrature angles and summing the inverted output with an output of the split-photodetector at the other of the pair of quadrature angles.

3. The method of claim 2, further comprising passing the reflected signal through an objective lens prior to measuring intensity using the split-photodetector.

4. The method of claim 3, wherein intensity measurement of the far-field diffraction pattern of the reflected beam is done in a Fourier plane.

5. The method of claim 1, wherein the substrate is a disk and scanning of the substrate is done by rotating the disk.

6. A quadrature interferometric method for determining the presence or absence of a target analyte in a sample, comprising:
using a laser beam having a wavelength $\lambda$ and a waist $w_o$ to probe at least a portion of a substrate having a reflecting surface that has been exposed to the sample, the reflecting surface including at least a first region having a layer of recognition molecules specific to the target analyte and a second region that does not include a layer of recognition molecules specific to the target analyte; and
measuring a time dependent intensity on a photodetector of a substantially only first quadrature at one of a pair of quadrature angles $\Theta_q$ of a reflected diffraction signal of the probe beam while probing the first region and the second region.

7. The method of claim 6, wherein the time dependence arises from a relative motion of the incident laser beam with respect to the substrate.

8. The method of claim 7, wherein the substrate is a disk and the relative motion of the disk with respect to the incident laser beam is generated by rotating the disk.

9. The method of claim 8, wherein the reflected diffraction signal of the laser beam is measured using a split-photodetector configuration, further comprising inverting a first output portion of the reflected signal corresponding to the one of the pair of quadrature angles, and summing the inverted first output with a second output of the reflected signal corresponding to the other of the pair of quadrature angles.

10. The method of claim 9, wherein the substrate is a disk and the reflected diffraction signal is passed through an objective lens prior to measuring the intensity.

11. The method of claim 7, further comprising passing the reflected diffraction signal of the probe beam through a $\pi/2$ phase mask prior to measuring the intensity.

12. The method of claim 6, wherein the reflecting surface is substantially flat and the quadrature angles are defined from a ray normal to the substrate by a formula:

$\Theta_q = \sin^{-1}(\lambda/2w_o)$.

13. The method of claim 6, wherein the substrate is a disk and the reflecting surface of the disk includes a plurality of lands and a plurality of ridges, the ridges having a height h, and the quadrature angles are defined from a ray normal to the substrate by a formula:

$\Theta_q = \sin^{-1}[(\lambda/2-4h)/w_o]$.

14. A phase-contrast quadrature interferometric step-detection method of determining the presence or absence of a target analyte in a sample, comprising:
measuring time dependent intensity of a far-field diffraction pattern of a reflected light signal resulting from a probe laser beam incident on a disk having a spatial pattern of recognition molecules using a split photodetector configuration, and
summing contributions from a first quadrature and a second opposing quadrature of the resulting light signal, the summing of the contributions being preceded by inversion of the contribution of the first quadrature.

15. The method of claim 14, wherein intensity is measured of the resulting light signal that is reflected from a reflecting surface of the disk.

16. The method of claim 15, wherein the split photodetector configuration is a split-ring photodetector.

17. The method of claim 15, wherein the split photodetector configuration is a quadrant photodetector.

18. The method of claim 15, wherein the split photodetector configuration includes a first and a second photodetector, the probe beam having a wavelength $\lambda$ and a waist $w_o$ incident on the disk, the first and second photodetectors measuring intensity at substantially a pair of quadrature angles $\Theta_q$, the quadrature angles being defined from a ray normal to the disk by a formula $\Theta_q = \sin^{-1}(\lambda/2w_o)$.

19. The method of claim 15, wherein time dependent intensity is measured by rotating the disk.

20. The method of claim 19, wherein the disk is rotating at about 80 Hz.

21. A phase-contrast quadrature interferometric step-detection method of determining the presence or absence of a target analyte in a sample, comprising:
measuring a time dependent difference at substantially a first quadrature interference angle of a first portion of a reflected light signal of a substantially only first quadrature, the reflected light signal resulting from tracing a laser beam across alternating regions of a specific antibody and a non-specific antibody on a planar array.

22. The method of claim 21, further comprising measuring a time dependent difference at substantially a second quadrature interference angle of a second portion of the reflected light signal of a substantially only second quadrature resulting from the tracing of the laser beam across alternating regions of the planar array.

23. The method of claim 22, further comprising
inverting a first output of the first portion of the reflected light signal; and
summing the inverted first output with a second output of the second portion of the reflected light signal.

24. A scale free label free quadrature interferometric step-detection method of determining the presence or absence of a target analyte in a sample, comprising:
using a focused laser beam having an incident waist $w_o$ and a wavelength $\lambda$ to scan a disk having a spatially patterned layer of receptor molecules specific to the target analyte, the layer having a substantially sharp layer edge; and
detecting intensity change in a far-field diffraction pattern caused by scanning the substantially sharp layer edge using a split photodetector configuration, the split photodetector configuration providing an output of the far-field diffraction pattern at substantially at least one of a pair of quadrature interference angles defined from a ray normal to the disk.

25. A quadrature interferometric method of determining the presence or absence of a target analyte in a sample, comprising:
measuring an output of a first photodetector aligned in an optical train to receive a substantially only first quadrature of a reflected light signal resulting from observing at substantially a first quadrature angle the reflected light signal resulting from a probe laser beam having a wavelength $\lambda$ and a waist $w_o$ incident on a planar array having at least one ridge defined by a layer of receptor molecules specific to the target analyte, wherein quadrature angles $\Theta_q$ are defined from a ray normal to the planar array by a formula: $\Theta_q = \sin^{-1}(\lambda/2w_o)$.

26. The method of claim 25, further comprising measuring an output of a second photodetector aligned in the optical train to receive a substantially only second opposing quadrature resulting from observing at substantially a second quadrature angle the reflected light signal.

27. The method of claim 26, further comprising
inverting the output of the first photodetector; and
summing the inverted output of the first photodetector with the output of the second photodetector.

28. The method of claim 26, wherein the optical train includes an objective lens.

29. The method of claim 28, wherein the first and second photodetectors are measuring the far-field diffraction pattern of the reflected light signal in a Fourier plane.

* * * * *